United States Patent
Luo et al.

(10) Patent No.: US 9,145,405 B2
(45) Date of Patent: Sep. 29, 2015

(54) OXADIAZOLE COMPOUND AND PREPARATION METHOD THEREOF, PHARMACEUTICAL COMPOSITION AND USE THEREOF

(71) Applicants: SHANGHAI JIAO TONG UNIVERSITY, Shanghai (CN); ZHEJIANG MEDICINE CO., LTD. XINCHANG PHARMACEUTICAL FACTORY, Zhejiang (CN)

(72) Inventors: Xianjin Luo, Shanghai (CN); Weidong Ye, Zhejiang (CN)

(73) Assignees: Shanghai Jiao Tong University, Shanghai (CN); Zhejiang Medicine Co., Ltd, Xinchang Pharmaceutical Factory, Zhejiang (CN)

( * ) Notice: Subject to any disclaimer, the term of this patent is extended or adjusted under 35 U.S.C. 154(b) by 0 days.

(21) Appl. No.: 14/358,281

(22) PCT Filed: Nov. 9, 2012

(86) PCT No.: PCT/CN2012/001511
§ 371 (c)(1),
(2) Date: Jul. 30, 2014

(87) PCT Pub. No.: WO2013/071693
PCT Pub. Date: May 23, 2013

(65) Prior Publication Data
US 2014/0350026 A1 Nov. 27, 2014

(30) Foreign Application Priority Data

Nov. 14, 2011 (CN) ............. 2011 1 0359961
Nov. 8, 2012 (CN) ............. 2012 1 0442608

(51) Int. Cl.
C07D 271/06 (2006.01)
A61K 31/4245 (2006.01)
C07D 417/12 (2006.01)
C07D 413/14 (2006.01)
C07D 413/12 (2006.01)
C07D 417/14 (2006.01)

(52) U.S. Cl.
CPC .......... *C07D 417/12* (2013.01); *A61K 31/4245* (2013.01); *C07D 271/06* (2013.01); *C07D 413/12* (2013.01); *C07D 413/14* (2013.01); *C07D 417/14* (2013.01)

(58) Field of Classification Search
CPC ................... C07D 271/06; A61K 31/4245
See application file for complete search history.

(56) References Cited

U.S. PATENT DOCUMENTS 5,786,383 A    7/1998  Clement

FOREIGN PATENT DOCUMENTS

| EP | 0371 438 | 6/1990 |
| EP | 0504 574 | 9/1992 |
| KR | 2009 0077 091 | 7/2009 |
| WO | 2004 0204 45 | 3/2004 |

OTHER PUBLICATIONS

Yurugi, S., et at; "Syntheses of Nitrogen Heterocyclic Compounds III Hypocholesterolemic 1, 2, 4-Oxadiazole Derivatives," Chemical & Pharmaceutical Bulletin, 1973, 21(8), 1641-50, ISSN: 0009-2363.
Compound: RN 1325833-45-1 Registry ED STN, stock date: Aug. 31, 2011. CN Benxonitrile, 4-[2-[4-(5-methyl-1, 2, 4-oxadiazol-3-yl)phenoxyl] ethoxy]-.
Compound: RN 1319852-84-0 Registry ED STN, stock date: Aug. 19, 2011. CN Morpholine, 4-[[4-[2-[4- (5-methyl-1, 2, 4-oxadiazol-3-yl)phenoxy]/0 ethoxy]phenyl]sulfonyl]-.
Compound: RN 1387766-46-2 Registry ED STN, stock date: Aug. 8, 2012. CN1, 2. 4-Oxacilazole, 5-methyl-3-[4-(2-phenoxyethoxy)pheflyl]-.
PCT/CN2012/001511, Filed: Nov. 9, 2012, 'Written Opinion of the International Searching Authority,' Applicant: Shanghai Jiao Tong University.

*Primary Examiner* — Rebecca Anderson
*Assistant Examiner* — Karen Cheng
(74) *Attorney, Agent, or Firm* — Daniel A. Thomson; Emerson Thomson Bennett, LLC

(57) ABSTRACT

The present invention provides an anti-Coxsackie virus oxadiazole compound as represented by formula (I), or the pharmaceutically acceptable salt thereof, a preparation method, a pharmaceutical composition, and use thereof, wherein R is $CH_3$ or $CF_3$; R' and R" are respectively H, alkyl or halogen; A is O or S; n is a number from 1 to 6; X is O, S or NH; Y is alkyl, unsubstituted cycloalkyl, mono-substituted cycloalkyl, disubstituted cycloalkyl, poly-substituted cycloalkyl, unsubstituted aryl, mono-substituted aryl, disubstituted aryl, poly-substituted aryl, unsubstituted 5-6 membered heterocyclyl, mono-substituted 5-6 membered heterocyclyl, disubstituted 5-6 membered heterocyclyl, or poly-substituted 5-6 membered heterocyclyl. Compared to prior art, the oxadiazole compound of the present invention has excellent anti-Coxsackie virus activity, lower toxicity and high safety.

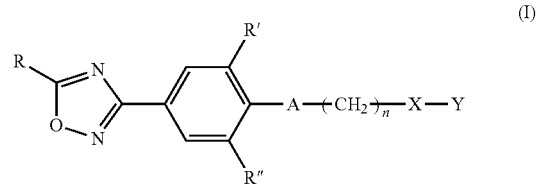

(I)

12 Claims, 6 Drawing Sheets

OXADIAZOLE COMPOUND AND PREPARATION METHOD THEREOF, PHARMACEUTICAL COMPOSITION AND USE THEREOF

FIELD OF THE INVENTION

The present invention relates to fields of synthesis of pharmaceutical compound, in particular, relates to oxadiazole compound, preparation method thereof, pharmaceutical composition comprising oxadiazole compound and use thereof.

Infectious diseases caused by enteroviruses have often occurred all over the world. The enteroviruses belong to picornaviridae comprising polio viruses, coxsackie viruses, enteric cytopathogenic human orphan virus(EHCO) and new enteroviruses. Bach viruses has many serums, at least more than 70types, which can violate many kinds of tissues such as nerves, cardiac muscles, muscles, skins and eye conjunctiva etc and can cause lots of infectious diseases all over the world. The picornavirus can violate many tissues and systems such as respiratory tracts, intestinal tracts, skins, muscles, hearts, livers, adrenal gland and central nervous systems. It makes clinical manifestations diversification. Common clinical symptoms include respiratory tract infection, herpanina, febrile rash, hand-foot-and-mouth disease, diarrhea of children, central nervous system syndrome, myocarditis and pericarditis, epidemic chest pain or epidemic myalgia, epidemic conjunctivitis, virus hepatitis and so on. In addition, rhinovirus and influenza virus belong to picornviridae, whose biological natures are similar to that of enteroviruses, This is the main viruses causing cold.

J. Med. Chem., 28: 748-752 (1985); 28:1906-1915(1985); 31:540-544(1988); 35:1002-1005 (1992), 4628-4633(1992); 36: 3240-3250 (1993); 37:2421-2436 (1994); 38:1355-1371 (1995) and U.S. Pat. No. 4,942,241 disclose the compounds as shown in Formula (II) and the anti-human rhinovirus activity thereof.

CN1687060A discloses the compound as shown in the following formula and the anti-influenza-viruses activity thereof.

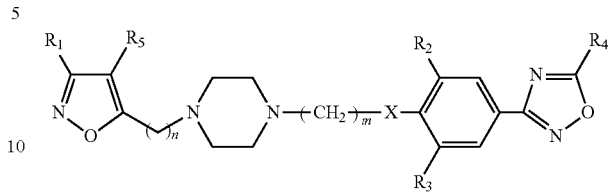

Wherein $R_1$ is alkyl, alkoxy, hydroxyl, cycloalkyl, hydroxyalky, alkoxyalkyl, hydroxyalkoxy, alkylthioalkyl, alkylsulfinylalkyl, alkylsulfonylalkyl, aminoalkyl, alkyl-substituted aminoalkyl, dialkyl-substituted aminoalkyl, alkoxycarbonyl, carboxyl or nitrilemethyl; $R_2$ and $R_3$ are respectively and independently H, alkyl, alkoxy, halogen, cyano, trichloromethyl or nitryl; $R_4$ is alkyl, alkoxy, hydroxyl, halomethyl, dihalomethyl, trihalomethyl, dihaloethyl, cycloalkyl, heterocyclyl, alkoxycarbonyl, hydroxyalkyl, alkoxyalkyl, alkylcarbonyloxy alkyl, cyano, halogen, thioalkyl, alkylthioalkyl, alkylthiol, sulfydryl, 2,2,2-trifluoroethyl, (4-methyl-phenyl) sulfonyloxy methyl, amino, alkyl-substituted amino, dialkyl-substituted amino, acylamino or N-alkyl-substituted acylamino; $R_5$ is H, halogen or alkyl; X is O or S; n=0-5; m=0-5.

At present, no medicine is used for the treatment of the diseases caused by coxsackie viruses. So it is urgent to find anti coxsackie-viruses activity compounds having better treatment effects, lower toxicity and better security and treat diseases caused by coxsackie viruses.

SUMMARY OF THE INVENTION

The purpose of the present invention is to provide oxadiazole compounds having use as anti-coxsackie and the pharmaceutically acceptable salts thereof as shown in Formula (I).

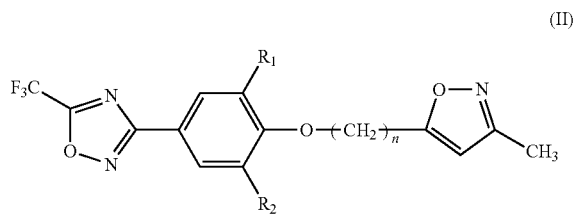

(II)

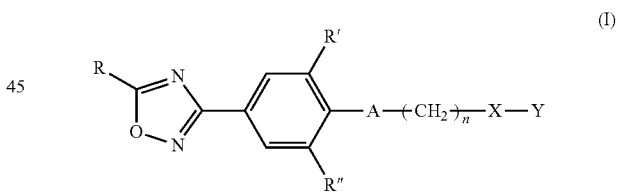

(I)

Wherein $R_1$ and $R_2$ are H, alkyl or halogen respectively; n=1-9; the compound of Formula (III) is the best anti-human rhinovirus activity. But it has not been sold on the market because of its greater toxicity.

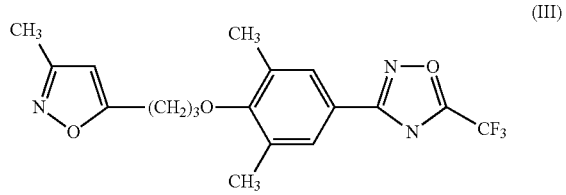

(III)

wherein, R is $CH_3$ or $CF_3$;
R' and R" are H, alkyl or halogen respectively;
A is O or S; n=1-6;
X is O, S or NH;
Y is alkyl, cycloalkyl, aryl or 5 to 6 membered heterocyclic group; wherein the alkyl is $C_1$-$C_6$ alkyl;
the cycloalkyl is unsubstituted $C_3$~$C_{10}$ cycloalkyl, monosubstituted $C_3$~$C_{10}$ cycloalkyl, disubstituted cycloalkyl, or polysubstituted $C_3$~$C_{10}$ cycloalkyl;
the aryl is unsubstituted phenyl, monosubstituted phenyl, disubstituted phenyl, or polysubstituted phenyl;
the 5 to 6 membered heterocyclic group is unsubstituted thienyl, unsubstituted furyl, unsubstituted pyrrolyl, unsubstituted isoxazolyl, unsubstituted oxazolyl, unsubstituted pyridazinyl, unsubstituted pyrazinyl, unsubstituted thiazolyl, unsubstituted isothiazolyl, unsubstituted triazolyl, unsubstituted tetrazolyl, unsubstituted thiadiazolyl, unsubstituted oxadiazolyl, unsubstituted imidazolyl, unsubstituted pyrazolyl, unsubstituted pyridyl, unsubstituted pyrimidinyl; or the 5 to 6 membered heterocyclic group is monosubstituted thienyl, monosubstituted furyl, monosubstituted pyrrolyl, monosubstituted isoxazolyl, monosubstituted oxazolyl, monosubstituted pyridazinyl, monosubstituted pyrazinyl, monosubstituted thiazolyl, monosubstituted isothiazolyl, monosubstituted triazolyl, monosubstituted tetrazolyl, monosubstituted thiadiazolyl, monosubstituted oxadiazolyl, monosubstituted imidazolyl, monosubstituted pyrazolyl, monosubstituted pyridyl, monosubstituted pyrimidinyl; or the 5 to 6 membered heterocyclic group is disubstituted thienyl, disubstituted furyl, disubstituted pyrrolyl, disubstituted isoxazoly, disubstituted oxazolyl, disubstituted pyridazinyl, disubstituted pyrazinyl, disubstituted thiazolyl, disubstituted isothiazolyl, disubstituted triazolyl, disubstituted imidazolyl, disubstituted pyrazolyl and disubstituted pyrimidinyl.

In the preferred embodiment of the present invention, the alkyl defined in R' and R" is methyl; n=2-3.

In the preferred embodiment of the present invention, the $C_1$-$C_6$ alkyl is ethyl, propyl, isopropyl or tert-butyl;

the $C_3$~$C_{10}$ cycloalkyl is cyclohexyl or adamantyl;

the monosubstituted phenyl, disubstituted phenyl, polysubstituted phenyl are respectively and independently phenyl substituted by $C_1$-$C_6$ alkyl, phenyl substituted by $C_1$-$C_6$ alkoxy, phenyl substituted by halogen, phenyl substituted by carboxyl, phenyl substituted by ester, phenyl substituted by nitro, phenyl substituted by cyanoo, or phenyl substituted by trihalomethyl;

the monosubstituted thienyl is thienyl substituted by C1-C6 alkyl; the monosubstituted furyl is furyl substituted by C1-C6 alkyl; the monosubstituted pyrrolyl is pyrrolyl substituted by C1-C6 alkyl; the monosubstituted isoxazolyl is isoxazolyl substituted by C1-C6 alkyl; the monosubstituted oxazolyl is oxazolyl substituted by C1-C6 alkyl; the monosubstituted pyridazinyl is pyridazinyl substituted by C1-C6 alkyl or halogen; the monosubstituted pyrazinyl is pyrazinyl substituted by halogen; the monosubstituted thiazolyl is thiazolyl substituted by C1-C6 alkyl; the monosubstituted isothiazolyl is isothiazolyl substituted by C1-C6 alkyl; the monosubstituted triazolyl is triazolyl substituted by C1-C6 alkyl; the monosubstituted tetrazolyl is tetrazolyl substituted by C1-C6 alkyl; the monosubstituted thiadiazolyl is thiadiazolyl substituted by C1-C6 alkyl; the monosubstituted oxadiazolyl is oxadiazolyl substituted by C1-C6 alkyl; the monosubstituted imidazolyl is imidazolyl substituted by C1-C6 alkyl; the monosubstituted pyrazolyl is pyrazolyl substituted by C1-C6 alkyl;

the monosubstituted pyridyl is pyridyl substituted by $C_1$-$C_6$ alkyl, pyridyl substituted by $C_1$-$C_6$ alkoxy, pyridyl substituted by halogen, pyridyl substituted by $C_1$-$C_6$ carboxyl, pyridyl substituted by $C_1$-$C_6$ ester group, pyridyl substituted by nitro, pyridyl substituted by cyano or pyridyl substituted by trihalomethyl.

the monosubstituted pyrimidinyl is pyrimidinyl substituted by $C_1$-$C_6$ alkyl, pyrimidinyl substituted by halogen, pyrimidinyl substituted by $C_1$-$C_6$ carboxyl, pyrimidinyl substituted by $C_1$-$C_6$ ester group, pyrimidinyl substituted by hydroxyl, pyrimidinyl substituted by cyano, or pyrimidinyl substituted by trihalomethyl;

the disubstituted thienyl is thienyl disubstituted by halogen; the disubstituted furyl is furyl disubstituted by halogen; the disubstituted pyrrolyl is pyrrolyl disubstituted by halogen; the disubstituted isoxazolyl is isoxazolyl disubstituted by halogen; the disubstituted oxazolyl is oxazolyl disubstituted by halogen; the disubstituted pyridazinyl is pyridazinyl disubstituted by halogen; the disubstituted pyrazinyl is pyrazinyl disubstituted by halogen; the disubstituted thiazolyl is thiazolyl disubstituted by halogen; the disubstituted isothiazolyl is isothiazolyl disubstituted by halogen; the disubstituted triazolyl is triazolyl disubstituted by halogen, disubstituted imidazolyl, disubstituted pyrazolyl.

In the preferred embodiments of the present invention, the phenyl substituted by C1~C6 alkoxy is phenyl substituted by methoxyl, phenyl substituted by ethoxyl or phenyl substituted by propoxy, the isoxazolyl substituted by C1-C6 alkyl is isoxazolyl substituted by trifluoromethyl, isoxazolyl substituted by methyl, isoxazolyl substituted by ethyl, isoxazolyl substituted by propyl or isoxazolyl substituted by isopropyl; the oxazolyl substituted by C1~C6 alkyl is oxazolyl substituted by methyl; the pyridazinyl substituted by C1~C6 alkyl is pyridazinyl substituted by methyl or pyridazinyl substituted by ethyl, the pyrazinyl substituted by halogen is pyrazinyl substituted by fluorine or pyrazinyl substituted by chlorine; the thiazolyl substituted by C1-C6 alkyl is thiazolyl substituted by methyl, thiazolyl substituted by ethyl, thiazolyl substituted by propyl or thiazolyl substituted by isopropyl; the isothiazolyl substituted by C1-C6 alkyl is isothiazolyl substituted by methyl, isothiazolyl substituted by ethyl, isothiazolyl substituted by propyl or isothiazolyl substituted by isopropyl; the triazolyl substituted by C1-C6 alkyl is triazolyl substituted by trifluoromethyl, triazolyl substituted by methyl or triazolyl substituted by ethyl; the tetrazolyl substituted by C1-C6 alkyl is tetrazolyl substituted by methyl; the thiadiazolyl substituted by C1-C6 alkyl is thiadiazolyl substituted by trifluoromethyl, thiadiazolyl substituted by methyl, thiadiazolyl substituted by ethyl or thiadiazolyl substituted by propyl; the oxadiazolyl substituted by C1-C6 alkyl is oxadiazolyl substituted by trifluoromethyl, oxadiazolyl substituted by methyl, oxadiazolyl substituted by ethyl or oxadiazolyl substituted by propyl; the imidazolyl substituted by C1-C6 alkyl is imidazolyl substituted by methyl, imidazolyl substituted by ethyl or imidazolyl substituted by propyl; the pyrazolyl substituted by C1-C6 alkyl is pyrazolyl substituted by trifluoromethyl, pyrazolyl substituted by methyl, pyrazolyl substituted by ethyl or pyrazolyl substituted by propyl.

In the preferred embodiment of the present invention, the pharmaceutically acceptable salt is inorganic acid salt, organic acid salt, inorganic alkali salt or organic alkali salt; the inorganic acid salt is selected from any one of the group consisting of hydrochloride, hydrobromide, hydriodate, sulfate, nitrate, phosphate, perchlorate or the combination thereof; the organic acid salt is selected from any one of the group consisting of tosilate, mesylate, acetate, trifluoroacetate, propionate, citrate, malonate, succinate, lactate, oxalate, tartrate, benzoate or the combination thereof; the inorganic alkali salt is alkaline-earth metal salt; the organic alkali salt is organic amine salt.

More preferably, the alkaline-earth metal salt is magnesium salt or calcium salt; the organic amine salt is morpholine salt, piperidine salt, trialkylamine salt, pyridine salt, dimethylamine salt or diethylamine salt.

In the more preferred embodiment of the present invention, the oxadiazole compound and pharmaceutically acceptable salt thereof as shown in Formula (I) are:
1) 3-[3,5-dimethyl-4-[2-(5-methylisoxazole-3-oxy)ethoxyl]phenyl]-5-(trifluoromethyl)-1,2,4-oxadiazole;
2) 3-[3,5-dimethyl-4-[2-(5-methylisoxazole-3-oxy)ethoxyl]phenyl]-5-methyl-1,2,4-oxadiazole;
3) 3-[3,5-dimethyl-4-[2-(5-trifluoromethylisoxazole-3-oxy)ethoxyl]phenyl]-5-(trifluoromethyl)-1,2,4-oxadiazole;

4) 3-[2-[2,6-dimethyl-4-[5-(trifluoromethyl)-1,2,4-oxadiazole-3-yl]phenoxyl]ethoxyl]-isoxazole-5-carboxylate;
5) 3-[3,5-dimethyl-4-[2-(3-trifluoromethylisoxazole-5-oxy)ethoxyl]phenyl]-5-(trifluoromethyl)-1,2,4-oxadiazole;
6) 3-[3,5-dimethyl-4-[3-(5-trifluoromethylisoxazole-3-oxy)propoxy]phenyl]-5-(trifluoromethyl)-1,2,4-oxadiazole;
7) 3-[3-[2,6-dimethyl-4-[5-(trifluoromethyl)-1,2,4-oxadiazole-3-yl]phenoxyl]propoxy]-isoxazole-5-carboxylate;
8) 3-[3,5-dimethyl-4-[3-(3-methylisoxazole-5-oxy)propoxy]phenyl]-5-(trifluoromethyl)-1,2,4-oxadiazole;
9) 3-[3,5-dimethyl-4-[3-(3-trifluoromethylisoxazole-5-oxy)propoxy] phenyl]-5-(trifluoromethyl)-1,2,4-oxadiazole;
10) 3-[3,5-dimethyl-4-[2-(5-methylisothiazole-3-oxy)ethoxyl]phenyl]-5-(trifluoromethyl)-1,2,4-oxadiazole;
11) 3-[3,5-dimethyl-4-[3-(5-methylisothiazole-3-oxy)propoxy]phenyl]-5-(trifluoromethyl)-1,2,4-oxadiazole;
12) 3-[3,5-dimethyl-4-[2-(4-methylimidazole-2-oxy)ethoxyl]phenyl]-5-(trifluoromethyl)-1,2,4-oxadiazole;
13) 3-[3,5-dimethyl-4-[2-(4-methylthiazole-2-oxy)ethoxyl]phenyl]-5-(trifluoromethyl)-1,2,4-oxadiazole;
14) 3-[3,5-dimethyl-4-[2-(4-methylthiazole-2-thio)ethoxyl]phenyl]-5-(trifluoromethyl)-1,2,4-oxadiazole;
15) 3-[3,5-dimethyl-4-[2-(3-methyl-1H-pyrazole-5-oxy)ethoxyl]phenyl]-5-(trifluoromethyl)-1,2,4-oxadiazole;
16) 3-[3,5-dimethyl-4-[2-[1-methyl-3-(trifluoromethyl)-1H-pyrazole-5-oxy]ethoxyl]phenyl]-5-(trifluoromethyl)-1,2,4-oxadiazole;
17) 5-[2-[2,6-dimethyl-4-[5-(trifluoromethyl)-1,2,4-oxadiazole-3-yl] phenoxyl]ethoxyl]-1-methyl-1H-pyrazole-3-carboxylic acid;
18) 3-[3,5-dimethyl-4-[2-(5-methyl-1H-imidazole-2-thio)ethoxyl]phenyl]-5-(trifluoromethyl)-1,2,4-oxadiazole;
19) 3-[2-[2,6-dimethyl-4-[5-(trifluoromethyl)-1,2,4-oxadiazole-3-yl]phenoxyl]ethoxyl]-5-methyl-1,2,4-oxadiazole;
20) 3-[2-[2,6-dimethyl-4-[5-(trifluoromethyl)-1,2,4-oxadiazole-3-yl]phenoxyl]propoxy]-5-methyl-1,2,4-oxadiazole;
21) 3-[3,5-dimethyl-4-[(4-(trifluoromethyl)-1,2,4-oxadiazole-2-oxy)ethoxyl]phenyl]-5-(trifluoromethyl)-1,2,4-oxadiazole;
22) 5-[3,5-dimethyl-4-[(2-(5-(trifluoromethyl)-1,2,4-oxadiazole-3-oxy)ethoxyl]phenyl]-3-(trifluoromethyl)-1,2,4-oxadiazole;
23) 3-[3,5-dimethyl-4-[2-(3-methyl-1,2,4-thiadiazole-5-thio)ethoxyl]phenyl]-5-(trifluoromethyl)-1,2,4-oxadiazole;
24) 3-[2-[2,6-dimethyl-4-[5-(trifluoromethyl)-1,2,4-oxadiazole-3-yl]phenoxyl]ethoxyl]-5-methyl-4H-1,2,4-triazole;
25) 3-[2-[2,6-dimethyl-4-[5-(trifluoromethyl)-1,2,4-oxadiazole-3-yl]phenoxyl]ethylthio]-5-methyl-4H-1,2,4-triazole;
26) 3-[2-[2,6-dimethyl-4-[5-(trifluoromethyl)-1,2,4-oxadiazole-3-yl]phenoxyl]ethylthio]-5-trifluoromethyl-4H-1,2,4-triazole;
27) 3-[2-[2,6-dimethyl-4-[5-(trifluoromethyl)-1,2,4-oxadiazole-3-yl]phenoxyl]ethylthio]-4,5-dimethyl-4H-1,2,4-triazole;
28) 3-[3,5-dimethyl-4-[2-[5-methyl-1,3,4-oxadiazole-2-oxy]ethoxyl]phenyl]-5-(trifluoromethyl)-1,2,4-oxadiazole;
29) 3-[3,5-dimethyl-4-[3-[5-methyl-1,3,4-oxadiazole-2-oxy]propylthio]phenyl]-5-(trifluoromethyl)-1,2,4-oxadiazole;
30) 3-[3,5-dimethyl-4-[2-[5-trifluoromethyl-1,3,4-thiadiazole-2-oxy]ethoxyl]phenyl]-5-(trifluoromethyl)-1,2,4-oxadiazole;
31) 3-[3,5-dimethyl-4-[2-[5-trifluoromethyl-1,3,4-thiadiazole-2-oxy]ethylthio]phenyl]-5-(trifluoromethyl)-1,2,4-oxadiazole;
32) 2-[2-[2,6-dimethyl-4-[5-(trifluoromethyl)-1,2,4-oxadiazole-3-yl]phenoxyl]ethoxyl]-4-hydroxyl-pyrimidine-5-carboxylic acid;
33) 2-[2-[2,6-dimethyl-4-[5-(trifluoromethyl)-1,2,4-oxadiazole-3-yl]phenoxyl]ethoxyl]-4-(trifluoromethyl) pyrimidine;
34) 2-[2-[2,6-dimethyl-4-[5-(trifluoromethyl)-1,2,4-oxadiazole-3-yl]phenoxyl]ethylthio]-4-(trifluoromethyl) pyrimidine;
35) 3-[3,5-dimethyl-4-[(2-(cyclohexyloxy)-ethoxyl)phenyl]-5-(trifluoromethyl)-1,2,4-oxadiazole;
36) 3-[3,5-dimethyl-4-[(2-tert-butoxy)ethoxyl]phenyl]-5-(trifluoromethyl)-1,2,4-oxadiazole;
37) 3-[3,5-dimethyl-4[(2-adamantanoxy)propoxy]phenyl]-5-(trifluoromethyl)-1,2,4-oxadiazole;
38) 4-[2,6-dimethyl-4-[(5-(trifluoromethyl)-1,2,4-oxadiazole-3-yl)phenoxyl]ethoxyl]-3-fluorobenzonitrile;
39) 3-[3,5-dimethyl-4-[(2-fluoro-4-methylphenoxyl)ethoxyl]phenyl]-5-(trifluoromethyl)-1,2,4-oxadiazole;
40) 3-[3,5-dimethyl-4-[(2-fluoro-4-methoxyphenoxyl)ethoxyl]phenyl]-5-(trifluoromethyl)-1,2,4-oxadiazole;
41) 3-[3,5-dimethyl-4-[(2-fluoro-4-nitrophenoxyl)ethoxyl]phenyl]-5-(trifluoromethyl)-1,2,4-oxadiazole;
42) 3-[3,5-dimethyl-4-[(2,6-dichlorophenoxyl)ethoxyl]phenyl]-5-(trifluoromethyl)-1,2,4-oxadiazole;
43) 3-[3,5-dimethyl-4-[(2,4-dichlorophenoxyl)ethoxyl]phenyl]-5-(trifluoromethyl)-1,2,4-oxadiazole;
44) 6-[2,6-dimethyl-4-[(5-(trifluoromethyl)-1,2,4-oxadiazole-3-yl)phenoxyl]ethoxyl]pyridine-2-oxy-ethylketoxime;
45) 5-[2,6-dimethyl-4-[(5-(trifluoromethyl)-1,2,4-oxadiazole-3-yl)phenoxyl]ethoxyl]pyridine-2-oxy-ethylketoxime;
46) 6-[2,6-dimethyl-4-[(5-(trifluoromethyl)-1,2,4-oxadiazole-3-yl)phenoxyl]ethoxyl]-5-fluoro-3-cyanopyridine;
47) 2-[2,6-dimethyl-4-[(5-(trifluoromethyl)-1,2,4-oxadiazole-3-yl)phenoxyl]ethoxyl]-3-fluoro-5-methylpyridine;
48) 6-[2,6-dimethyl-4-[(5-(trifluoromethyl)-1,2,4-oxadiazole-3-yl)phenoxyl]ethoxyl]-5-fluoro-2-hydroxyl-3-cyanopyridine;
49) 6-[2,6-dimethyl-4-[(5-(trifluoromethyl)-1,2,4-oxadiazole-3-yl) phenoxyl]ethoxyl]-5-fluoro-3-pyridinecarboxylate;
50) 6-[2,6-dimethyl-4-[(5-(trifluoromethyl)-1,2,4-oxadiazole-3-yl)phenoxyl]ethoxyl]-3-cyanopyridine;
51) 6-[2,6-dimethyl-4-[(5-(trifluoromethyl)-1,2,4-oxadiazole-3-yl)phenoxyl]ethoxyl]-5-methylpyridine;
52) 6-[2,6-dimethyl-4-[(5-(trifluoromethyl)-1,2,4-oxadiazole-3-yl)phenoxyl]ethoxyl]-5-trifluoromethylpyridine;
53) 4-[2,6-dimethyl-4-[(5-(trifluoromethyl)-1,2,4-oxadiazole-3-yl)phenoxyl]ethoxyl]-2-hydroxyl-5-fluoropyrimidine;
54) 4-[2,6-dimethyl-4-[(5-(trifluoromethyl)-1,2,4-oxadiazole-3-yl)phenoxyl]ethoxyl]-2-methoxyl-5-fluoropyrimidine;
55) 3-[2-(2,6-dimethyl-4-[(5-(trifluoromethyl)-1,2,4-oxadiazole-3-yl)phenoxyl]ethoxyl]-2-formamide-6-fluoropyrazine;
56) 3-[2,6-dimethyl-4-[(5-(trifluoromethyl)-1,2,4-oxadiazole-3-yl)phenoxyl]ethoxyl]-6-methylpyridazine;
57) 3-[3,5-dimethyl-4-[2-(5-trifluoromethylisoxazole-3-oxy)ethoxyl]phenyl]-5-(trifluoromethyl)-1,2,4-oxadiazole;

58) 3-[2-[2,6-dimethyl-4-[5-(trifluoromethyl)-1,2,4-oxadiazole-3-yl]phenoxyl]ethoxyl]isoxazole-5-carboxylate;
59) 3-[3,5-dimethyl-4-[2-(3-trifluoromethylisoxazole-5-oxy)ethoxyl]phenyl]5-(trifluoromethyl)-1,2,4-oxadiazole;
60) 3-[3,5-dimethyl-4-[3-(5-trifluoromethylisoxazole-3-oxy)propoxy]phenyl]-5-(trifluoromethyl)-1,2,4-oxadiazole;
61) 3-[3-[2,6-dimethyl-4-[5-(trifluoromethyl)-1,2,4-oxadiazole-3-yl]phenoxyl]propoxy]isoxazole-5-carboxylate;
62) 3-[3,5-dimethyl-4-[3-(3-methylisoxazole-5-oxy)propoxy]phenyl]-5-(trifluoromethyl)-1,2,4-oxadiazole;
63) 3-[3,5-dimethyl-4-[3-(3-trifluoromethylisoxazole-5-oxy)propoxy]phenyl]-5-(trifluoromethyl)-1,2,4-oxadiazole;
64) 3-[3,5-dimethyl-4-[2-(5-methylisothiazole-3-oxy)ethoxyl] phenyl]-5-(trifluoromethyl)-1,2,4-oxadiazole;
65) 3-[3,5-dimethyl-4-[3-(5-methylisothiazole-3-oxy)propoxy]phenyl]-5-(trifluoromethyl)-1,2,4-oxadiazole;
66) 3-[3,5-dimethyl-4-[2-(4-methylimidazole-2-oxy)ethoxyl]phenyl]-5-(trifluoromethyl)-1,2,4-oxadiazole;
67) 3-[3,5-dimethyl-4-[2-(4-methylthiazole-2-oxy)ethoxyl]phenyl]-5-(trifluoromethyl)-1,2,4-oxadiazole;
68) 3-[3,5-dimethyl-4-[2-(4-methylthiazole-2-thio)ethoxyl]phenyl]-5-(trifluoromethyl)-1,2,4-oxadiazole;
69) 3-[3,5-dimethyl-4-[2-(3-methyl-1H-pyrazole-5-oxy)ethoxyl]phenyl]-5-(trifluoromethyl)-1,2,4-oxadiazole;
70) 3-[3,5-dimethyl-4-[2-[1-methyl-3-(trifluoromethyl)-1H-pyrazole-5-oxy]ethoxyl]phenyl]-5-(trifluoromethyl)-1,2,4-oxadiazole;
71) 5-[2-[2,6-dimethyl-4-[5-(trifluoromethyl)-1,2,4-oxadiazole-3-yl]phenoxyl]ethoxyl]-1-methyl-1H-pyrazole-3-carboxylic acid;
72) 3-[3,5-dimethyl-4-[2-(5-methyl-1H-imidazole-2-oxy)ethoxyl]phenyl]-5-(trifluoromethyl)-1,2,4-oxadiazole;
73) 3-[2-[2,6-dimethyl-4-[5-(trifluoromethyl)-1,2,4-oxadiazole-3-yl]phenoxyl]ethoxyl]-5-methyl-1,2,4-oxadiazole;
74) 3-[3-[2,6-dimethyl-4-[5-(trifluoromethyl)-1,2,4-oxadiazole-3-yl]phenoxyl]propoxy]-5-methyl-1,2,4-oxadiazole;
75) 3-[3,5-dimethyl-4-[(4-(trifluoromethyl)-1,2,4-oxadiazole-2-oxy)ethoxyl]phenyl]-5-(trifluoromethyl)-1,2,4-oxadiazole;
76) 5-[3,5-dimethyl-4-[2-(5-(trifluoromethyl)-1,2,4-oxadiazole-3-oxy)ethoxyl]phenyl]-5-(trifluoromethyl)-1,2,4-oxadiazole;
77) 3-[3,5-dimethyl-4-[2-(3-methyl-1,2,4-thiadiazole-5-thio)ethoxyl]phenyl]-5-(trifluoromethyl)-1,2,4-oxadiazole;
78) 3-[2-[2,6-dimethyl-4-[5-(trifluoromethyl)-1,2,4-oxadiazole-3-yl]phenoxyl]ethoxyl]-5-methyl-4H-1,2,4-triazole;
79) 3-[2-[2,6-dimethyl-4-[5-(trifluoromethyl)-1,2,4-oxadiazole-3-yl]phenoxyl]ethylthio]-5-methyl-4H-1,2,4-triazole;
80) 3-[2-[2,6-dimethyl-4-[5-(trifluoromethyl)-1,2,4-oxadiazole-3-yl]phenoxyl]ethylthio]-5-trifluoromethyl-4H-1,2,4-triazole;
81) 3-[2-[2,6-dimethyl-4-[5-(trifluoromethyl)-1,2,4-oxadiazole-3-yl]phenoxyl]ethylthio]-4,5-dimethyl-4H-1,2,4-triazole;
82) 3-[3,5-dimethyl-4-[2-[5-methyl-1,3,4-oxadiazole-2-oxy]ethoxyl] phenyl]-5-(trifluoromethyl)-1,2,4-oxadiazole;
83) 3-[3,5-dimethyl-4-[3-[5-methyl-1,3,4-oxadiazole-2-oxy]propylthio]phenyl]-5-(trifluoromethyl)-1,2,4-oxadiazole;
84) 3-[3,5-dimethyl-4-[2-[5-trifluoromethyl-1,3,4-thiadiazole-2-oxy]ethoxyl]phenyl]-5-(trifluoromethyl)-1,2,4-oxadiazole;
85) 3-[3,5-dimethyl-4-[2-[5-trifluoromethyl-1,3,4-thiadiazole-2-oxy]ethylthio]phenyl]-5-(trifluoromethyl)-1,2,4-oxadiazole;
86) 2-[2-[2,6-dimethyl-4-[5-(trifluoromethyl)-1,2,4-oxadiazole-3-yl]phenoxyl]ethoxyl]-4-hydroxyl-pyrimidine-5-carboxylic acid;
87) 2-[2-[2,6-dimethyl-4-[5-(trifluoromethyl)-1,2,4-oxadiazole-3-yl]phenoxyl]ethoxyl]-4-(trifluoromethyl)pyrimidine;
88) 2-[2-[2,6-dimethyl-4-[5-(trifluoromethyl)-1,2,4-oxadiazole-3-yl]phenoxyl]ethylthio]-4-(trifluoromethyl)pyrimidine;
89) 3-[3,5-dimethyl-4-[2-(cyclohexyloxy)ethoxyl]phenyl]-5-(trifluoromethyl)-1,2,4-oxadiazole;
90) 3-[3,5-dimethyl-4-[(2-tert-butoxy)ethoxyl]phenyl]-5-(trifluoromethyl)-1,2,4-oxadiazole;
91) 3-[3,5-dimethyl-4-[(2-adamantanoxy)propoxy]phenyl]-5-(trifluoromethyl)-1,2,4-oxadiazole;
92) 4-[2,6-dimethyl-4-[(5-(trifluoromethyl)-1,2,4-oxadiazole-3-yl)phenoxyl]ethoxyl]-3-fluorobenzonitrile;
93) 3-[3,5-dimethyl-4-[(2-fluoro-4-methylphenoxyl) ethoxyl]phenyl]-5-(trifluoromethyl)-1,2,4-oxadiazole;
94) 3-[3,5-dimethyl-4-[(2-fluoro-4-methoxyphenoxyl) ethoxyl]phenyl]-5-(trifluoromethyl)-1,2,4-oxadiazole;
95) 3-[3,5-dimethyl-4-[(2-fluoro-4-nitrophenoxyl)ethoxyl] phenyl]-5-(trifluoromethyl)-1,2,4-oxadiazole;
96) 3-[3,5-dimethyl-4-[(2,6-dichlorophenoxyl)ethoxyl]phenyl]-5-(trifluoromethyl)-1,2,4-oxadiazole;
97) 3-[3,5-dimethyl-4-[(2,4-dichlorophenoxyl)ethoxyl]phenyl]-5-(trifluoromethyl)-1,2,4-oxadiazole;
98) 6-[2,6-dimethyl-4-[(5-(trifluoromethyl)-1,2,4-oxadiazole-3-yl)phenoxyl]ethoxyl]pyridine-2-oxy-ethylketoxime;
99) 5-[2,6-dimethyl-4-[(5-(trifluoromethyl)-1,2,4-oxadiazole-3-yl)phenoxyl]ethoxyl]pyridine-2-oxy-ethylketoxime;
100) 6-[2,6-dimethyl-4-[(5-(trifluoromethyl)-1,2,4-oxadiazole-3-yl)phenoxyl]ethoxyl]-5-fluoro-3-cyanopyridine;
101) 2-[2,6-dimethyl-4-[(5-(trifluoromethyl)-1,2,4-oxadiazole-3-yl)phenoxyl]ethoxyl]-3-fluoro-5-methylpyridine;
102) 6-[2,6-dimethyl-4-[(5-(trifluoromethyl)-1,2,4-oxadiazole-3-yl)phenoxyl]ethoxyl]-5-fluoro-2-hydroxy-3-cyanopyridine;
103) 6-[2,6-dimethyl-4-[(5-(trifluoromethyl)-1,2,4-oxadiazole-3-yl)phenoxyl]ethoxyl]-5-fluoro-3-pyridinecarboxylate;
104) 6-[2,6-dimethyl-4-[(5-(trifluoromethyl)-1,2,4-oxadiazole-3-yl)phenoxyl]ethoxyl]-3-cyanopyridine;
105) 6-[2,6-dimethyl-4-[(5-(trifluoromethyl)-1,2,4-oxadiazole-3-yl)phenoxyl]ethoxyl]-5-methylpyridine;
106) 6-[2,6-dimethyl-4-[(5-(trifluoromethyl)-1,2,4-oxadiazole-3-yl)phenoxyl]ethoxyl]-5-trifluoromethylpyridine;
107) 4-[2,6-dimethyl-4-(5-(trifluoromethyl)-1,2,4-oxadiazole-3-yl) phenoxyl]ethoxyl]-2-hydroxy-5-fluoropyrimidine;
108) 4-[2,6-dimethyl-4-[(5-(trifluoromethyl)-1,2,4-oxadiazole-3-yl)phenoxyl]ethoxyl]-2-methoxyl-5-fluoropyrimidine;
109) 3-[2-(2,6-dimethyl-4-[(5-(trifluoromethyl)-1,2,4-oxadiazole-3-yl)phenoxyl]ethoxyl]-2-formamide-6-fluoropyrazine;
110) 3-[2,6-dimethyl-4-[(5-(trifluoromethyl)-1,2,4-oxadiazole-3-yl)phenoxyl]ethoxyl]-6-methylpyridazine;

111) 3-[3,5-dimethyl-4-[2-[4-(5-methyl-1,2,4-oxadiazole-3-yl)phenoxyl]ethoxyl]phenyl]-5-(trifluoromethyl)-1,2,4-oxadiazole;
112) 3-[3,5-dimethyl-4-[2-[4-[5-(trifluoromethyl)-1,2,4-oxadiazole-3-yl]phenoxyl]ethoxyl]phenyl]-5-(trifluoromethyl)-1,2,4-oxadiazole;
113) 2-[2-[2,6-dimethyl-4-[5-(trifluoromethyl)-1,2,4-oxadiazole-3-yl]phenoxyl]ethoxyl]-5-(5-methyl-1,2,4-oxadiazole-3-yl)-pyridine;
114) 2-[2-[2,6-dimethyl-4-[5-(trifluoromethyl)-1,2,4-oxadiazole-3-yl]phenoxyl]ethoxyl]-5-[5-(trifluoromethyl)-1,2,4-oxadiazole-3-yl]-pyridine;
115) 2-[2-[2,6-dimethyl-4-[5-(trifluoromethyl)-1,2,4-oxadiazole-3-yl]phenoxyl]ethoxyl]-3-fluoro-5-(5-methyl-1,2,4-oxadiazole-3-yl)-pyridine;
116) 2-[2-[2,6-dimethyl-4-[5-(trifluoromethyl)-1,2,4-oxadiazole-3-yl]phenoxyl]ethoxyl]-3-fluoro-5-[5-(trifluoromethyl)-1,2,4-oxadiazole-3-yl]-pyridine;
117) 3-[3,5-dimethyl-4-[3-[4-(5-methyl-1,2,4-oxadiazole-3-yl)phenoxyl] propoxyl]phenyl]-5-(trifluoromethyl)-1,2,4-oxadiazole;
118) 3-[3,5-dimethyl-4-[3-[4-[5-(trifluoromethyl)-1,2,4-oxadiazole-3-yl]phenoxyl]propoxyl]phenyl]-5-(trifluoromethyl)-1,2,4-oxadiazole;
119) 2-[3-[2,6-dimethyl-4-[5-(trifluoromethyl)-1,2,4-oxadiazole-3-yl]phenoxyl]propoxyl]-5-(5-methyl-1,2,4-oxadiazole-3-yl]-pyridine;
120) 2-[3-[2,6-dimethyl-4-[5-(trifluoromethyl)-1,2,4-oxadiazole-3-yl]phenoxyl]propoxyl]-3-fluoro-5-[5-(trifluoromethyl)-1,2,4-oxadiazole-3-yl]-pyridine;
121) 2-[3-[2,6-dimethyl-4-[5-(trifluoromethyl)-1,2,4-oxadiazole-3-yl]phenoxyl]propoxyl]-3-fluoro-5-(5-methyl-1,2,4-oxadiazole-3-yl)-pyridine;
122) 2-[3-[2,6-dimethyl-4-[5-(trifluoromethyl)-1,2,4-oxadiazole-3-yl]phenoxyl]propoxyl]-3-fluoro-5-[5-(trifluoromethyl)-1,2,4-oxadiazole-3-yl]-pyridine;
123) 3-[4-[2-[2-fluoro-4-[5-(trifluoromethyl)-1,2,4-oxadiazole-3-yl]phenoxyl]ethoxyl]-3,5-dimethyl-phenyl]-5-[5-(trifluoromethyl)-1,2,4-oxadiazole;
124) 3-[4-[3-[2-fluoro-4-[5-(trifluoromethyl)-1,2,4-oxadiazole-3-yl]phenoxyl]propoxyl]-3,5-dimethyl-phenyl]-5-[5-(trifluoromethyl)-1,2,4-oxadiazole;
125) 3-[3,5-dimethyl-4-[3-[5-(5-methylthiophene-2-oxy)phenoxyl]propoxyl]phenyl]-5-(trifluoromethyl)-1,2,4-oxadiazole;
126) 3-[3,5-dimethyl-4-[3-[5-(5-methylfuran-2-oxy)phenoxyl]propoxyl]phenyl]-5-(trifluoromethyl)-1,2,4-oxadiazole;
127) 3-[3,5-dimethyl-4-[3-[5-(5-methylpyrrole-2-oxy)phenoxyl]propoxyl]phenyl]-5-(trifluoromethyl)-1,2,4-oxadiazole;
128) 5-[2-[2,6-dimethyl-4-[5-(trifluoromethyl)-1,2,4-oxadiazole-3-yl]phenoxyl]ethoxyl]-1-methyl-tetrazole;
129) 3-[4-[3-[3,4-dimethylcyclohexyloxy]propoxy]-3,5-dimethylphenyl]-5-(trifluoromethyl)-1,2,4-oxadiazole;
130) 3-[4-[3-[2,6-dichloro-4-methylphenoxyl]propoxy]-3,5-dimethylphenyl]-5-(trifluoromethyl)-1,2,4-oxadiazole;
131) 2-cyano-5-[3-[2,6-dimethyl-4-[5-(trifluoromethyl)-1,2,4-oxadiazole-3-yl]phenoxyl]propoxy]pyrazine;
132) 2-[3-[2,6-dimethyl-4-[5-(trifluoromethyl)-1,2,4-oxadiazole-3-yl]phenoxyl]propoxy]-5-cyano-pyrimidine;
133) 3-cyano-6-[3-[2,6-dimethyl-4-[5-(trifluoromethyl)-1,2,4-oxadiazole-3-yl]phenoxyl]propoxy]pyridazine;
134) 2-[3-[2,6-dimethyl-4-[5-(trifluoromethyl)-1,2,4-oxadiazole-3-yl]phenoxyl]propoxy]-5-nitropyridine;
135) 2-[5-(trifluoromethyl)-1,2,4-oxadiazole-3-yl]-5-[3-[2,6-dimethyl-4-[5-(trifluoromethyl)-1,2,4-oxadiazole-3-yl]phenoxyl]propoxy]pyrazine;
136) 2-[3-[2,6-dimethyl-4-[5-(trifluoromethyl)-1,2,4-oxadiazole-3-yl]phenoxyl]propoxy]-5-[5-(trifluoromethyl)-1,2,4-oxadiazole-3-yl]-pyrimidine;
137) 3-[5-(trifluoromethyl)-1,2,4-oxadiazole-3-yl]-6-[3-[2,6-dimethyl-4-[5-(trifluoromethyl)-1,2,4-oxadiazole-3-yl]phenoxyl]propoxy]pyridazine.

Another purpose of the present invention is to provide a method of preparing for the oxadiazole compound and the pharmaceutically acceptable salt thereof as shown in formula (I), comprising the following steps:

1) compound of formula (Ia) is condensed with haloalkane in the presence of alkali to produce the compound of formula (Ib), wherein, the alkali is selected from any one of the group consisting of potassium carbonate, sodium carbonate, cesium carbonate, sodium hydroxide, potassium hydroxide, lithium hydroxide and cesium hydroxide, or the combination thereof

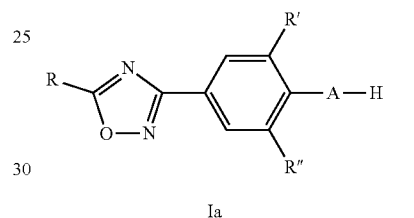

Ia

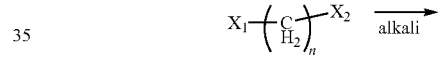

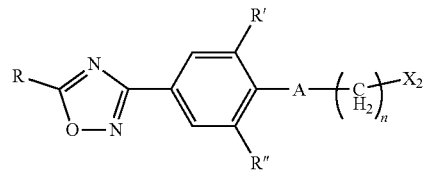

Ib 2) the compound of formula (Ib) is condensed with heterocyclic compound comprising hydroxy or sulfydryl in the presence of alkali to produce compound as shown in Formula (I), wherein the alkali is selected from any one of the group consisting of potassium carbonate, sodium carbonate, cesium carbonate, sodium hydroxide, potassium hydroxide, lithium hydroxide and cesium hydroxide, or the combination thereof;

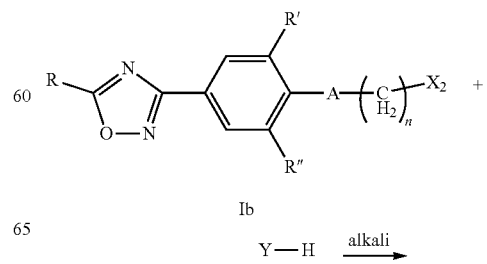

Ib

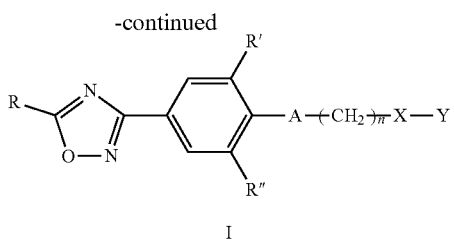

I wherein $X_1$ and $X_2$ in step 1) or 2) are Cl or Br; the definition of R, R', R", A, n, X and Y are the same as that of the oxadiazole compound as shown in Formula (I) and the pharmaceutically acceptable salt thereof.

Another purpose of the present invention is to provide the pharmaceutical composition having use as anti-coxsackie the pharmaceutical composition comprises a therapeutically effective amount of the oxadiazole compound or the pharmaceutically acceptable salt thereof of the present invention and the pharmaceutically acceptable carriers.

In the preferred embodiment of the present invention, the pharmaceutical composition can be administrated intestinally (such as oral or rectal), locally or parenterally, such as oral, injection, embedding, topical, spray, inhalation, etc.

In the preferred embodiment of the present invention, the oral pharmaceutical composition is selected from any one of the group consisting of tablet (conventional tablet, lozenge, sublingual tablet, buccal tablet, chewable tablet, dispersible tablet, soluble tablet, effervescent tablet, vaginal tablet or vaginal effervescent tablet, sustained release tablet, controlled release tablet, enteric-coated tablet, oral immediate-release tablet, etc), capsule (hard capsule, soft capsule, sustained-release capsule, controlled-release capsule, enteric coated capsule, etc), pill (dropping pill, sugar pill, pellet), oral liquid preparation (syrup, suspensions, oral solution, oral suspension, oral emulsion, syrups, mixture, distillate medicinal water or medicinal tea), granule (suspension granule, effervescent granule, enteric granule, sustained-release granule, controlled-release granule, etc.) and powder.

In the preferred embodiment of the present invention, the injection is selected from any one of the group consisting of parenteral solution, sterile powder for injection or sterile lump for injection (comprising processes such as solvent crystallization, spray drying or freeze-drying, etc.), transfusion, concentrated solution for injection.

In the preferred embodiment of the present invention, the external formulation is selected from any one of the group consisting of suppository, aerosol, dry powder inhalation, spray, film agent, gel, patch, glue agent, emplastrum, plaster, ointment, liniment, lotion, liniment and gel paste.

In the preferred embodiment of the present invention, the composition of the present invention can be manufactured by regular preparation techniques to those skilled in the art.

In the preferred embodiment of the present invention, the pharmaceutical composition is inclusion formulation or dispersion formulation.

In the preferred embodiment of the present invention, the pharmaceutically acceptable carriers are common excipients or adjuvant materials to those skilled in the art for the preparation of the above-mentioned formulation. The excipients or adjuvant materials commonly used in oral formulations or external formulations comprise but not limited to fillers or diluent, lubricants or glidants or antiadherent, dispersants, wetting agents, adhesives, modulator, solubilizers, antioxidants, bacteriostatic agent, emulsifiers, etc. Adhesives, such as syrup, acacia, gelatine, sorbitol, tragacanth, cellulose and its derivatives, gelatin mucilage, syrup, starch slurry or polyvinylpyrrolidone, preferably, the cellulose derivatives are microcrystalline cellulose, sodium carboxymethyl cellulose, ethyl cellulose or hydroxypropyl methyl cellulose; fillers, such as lactose, powdered sugar, dextrin, starch and its derivatives, cellulose and its derivatives, inorganic calcium salts, sorbitol alcohol or glycine, preferably, the inorganic calcium salts are calcium sulfate, calcium phosphate, calcium hydrophosphate or precipitated calcium carbonate; lubricants, such as siliciidoxydum, magnesium stearate, talcum powders, aluminum hydroxide, boric acid, hydrogenated vegetable oils, polyethylene glycol; disintegrating agent, such as starch and its derivatives, polyvinylpyrrolidone or microcrystalline cellulose, preferably, the starch derivatives are selected from any one of the group consisting of sodium carboxymethyl starch, sodium starch glycolate, amylum pregelatinisatum, modified starch, hydroxypropyl starch or corn starch; humectant, such as sodium dodecyl sulfate, water or alcohol and the like; preferably, the pharmaceutically acceptable carriers are selected from any one of the group consisting of cyclodextrin (α-cyclodextrin, β-cyclodextrin or γ-cyclodextrin), Celldone 102 CG, Polyplasdone XL-10, talcum powder, magnesium stearate, ethanol, etc.

In the preferred embodiment of the present invention, the excipients or adjuvant materials commonly used in injections of the present invention include, but are not limited to that of antioxidant such as sodium thiosulfate, sodium sulfite, sodium bisulfite, dibutyl benzoic acid, sodium metabisulfite, etc.; bacteriostatic agent such as 0.5 wt. % phenol, 0.3 wt. % cresol, 0.5 wt. % trichloro-tert-butanol; pH value regulator such as hydrochloric acid, citric acid, potassium(sodium) hydroxide, sodium citrate, buffer agent (such as sodium dihydrogen phosphate and disodium hydrogen phosphate); emulsifier such as polysorbate-80, sorbitan oleate, Pluronic F-68, lecithin, soybean phospholipid; solubilizer such as Tween-80, glycerine, etc.

In the preferred embodiment of the present invention, the active ingredient can also be mixed with pharmaceutically acceptable sustained/controlled release carriers according to the preparation requirement to produce pellets such as sustained-release pellets or controlled-release pellets, according to common preparation method of sustained/controlled release formulation to those skill in the art, for example, after adding blockers coating or microencapsulated the active ingredients; the sustained/controlled release carriers include but are not limited to oleaginous dopants, hydrophilic colloids or coating blockers, etc., the oleaginous dopant is selected from the group consisting of glyceryl monostearate, hydrogenated castor oil, mineral oil, polysiloxane or dimethylsiloxane; the hydrophilic colloid is derivations of cellulose such as sodium carboxymethylcellulose, hydroxypropyl cellulose, hydroxypropyl methyl cellulose, etc., or PVP, arabic gum, tragacanth, carbopol, etc.; the coating blocker is selected from the group consisting of ethylcellulose (EC), hydroxypropyl methyl cellulose (HMPC), polyvinylpyrrolidone (PVP), cellulose acetate-phthalate (CAP), acrylic resin, etc.

In the preferred embodiment of the present invention, according to needed administration method, the pharmaceutically acceptable composition comprises about 1-99 wt. % of any one of the compounds as shown in formula (I), compounds 1~137 or pharmaceutically acceptable salt thereof, or the pharmaceutically acceptable ester thereof, or the combination thereof, and about 1-99 wt. % of suitable pharmaceutically acceptable carriers.

In the preferred embodiment of the present invention, the pharmaceutical composition comprises about 5-75 wt. % of any one of the compounds as shown in Formula (I), compounds 1~137 or the pharmaceutically acceptable salt thereof, or the pharmaceutically acceptable ester thereof, or the combination thereof, the residual is the pharmaceutically acceptable carrier.

A further purpose of the present invention is to provide a use of oxadiazole compound or pharmaceutically acceptable salt thereof or pharmaceutically acceptable ester thereof or pharmaceutical composition thereof for preparation of the anti coxsackie-viruses medications.

In the preferred embodiment of the present invention, the anti coxsackie-viruses medications are used for the prophylaxis and treatment of any one of the group consisting of respiratory tract infection, heipangina, febrile rash, hand-foot-and-mouth disease, diarrhea of children, central nervous system syndrome, myocarditis, pericarditis, epidemic chest pain or myalgia, epidemic conjunctivitis, virus hepatitis, cold and other diseases or the combination thereof.

In the preferred embodiment of the present invention, the administration dosage of oxadiazole compound or the pharmaceutically acceptable salt or the pharmaceutically acceptable ester or the pharmaceutical composition in the present invention is about 10-500mg per day, preferably, 20-300mg per day when being used for anti coxsackie viruses.

In order to clearly express the protection scope of the present invention, the following items are defined as follows.

The "C1-C6 alkyl" in the present invention comprises linear chain or branched chain lower alkyl having 1-6 carbon atoms, such as methyl, ethyl, propyl, isopropyl, butyl, isobutyl, sec-butyl, tert-butyl, pentyl, tert-pentyl, hexyl, etc.

The "$C_1$-$C_6$ alkoxy" in the present invention comprises methoxy, ethoxy, propoxy, iso-propoxy, butoxyl, iso-butoxyl, tert-butoxy, pentyloxy, tert-pentyloxy or hexyloxy, etc.

The "$C_1$-$C_{12}$ alkylene" in the present invention comprises linear chain alkylene having carbon atoms of 1-12, preferably, alkylene with carbon atoms of 1-6, such as methylene, ethylidene, 1,3-propylidene, 1,4-butylidene, 1,5-pentylidene or 1,6-hexylidene.

The "phenylene, biphenylene, triphenylene", "cyclohexylene, cyclopentylene" in the present invention refer to a substituted group comprising two linkages, such as, phenylene comprising 1,2-phenylene, 1,3-phenylene, 1,4-phenylene, cyclohexylene comprising 1,2-cyclohexylene, 1,3-cyclohexylene, 1,4-cyclohexylene; cyclopentylene comprising 1,2-cyclopentylene or 1,3-cyclopentylene.

The "aryl" in the present invention comprises phenyl, naphthyl, etc., and the aryl may have one or more (preferably 1-3) suitable substituted group, such as, halogen, nitrile group, amino, $C_1$-$C_6$ alkyl, $C_1$-$C_6$ alkoxy, mono-(or bi- or tri-) halogenated (lower) alkyl, etc.

The "heteroaryl" in the present invention refers to 5-membered aromatic ring or 6-membered aromatic ring comprising one, two, three or four heteroatoms, such as nitrogen, oxygen or sulphur, and the ring having aryl ring, cycloalkyl ring, heteroaryl ring or heterocyclic alkyl ring (such as, benzothiophenyl, indolyl), and comprising N-oxide.

The heteroaryl may be 1-4 substituted group, the suitable substituted group is halogen, nitrile group, amino, $C_1$-$C_6$ alkyl, $C_1$-$C_6$ alkoxy, mono- (or bi- or tri-) halogenated (lower) alkyl, etc.

The "cycloalkyl" in the present invention refers to saturated or partially unsaturated carbon ring of 4-membered, 5-membered, 6-membered or 7-membered, the ring may be substituted by a suitable substituted group such as, halogen, nitrile, amino, $C_1$-$C_6$ alkyl, $C_1$-$C_6$ alkoxy, mono-(or bi- or tri-) halogenated (lower) alkyl, etc.

The "heterocyclic alkyl" or "heterocyclic ring" refers to saturated or partially unsaturated ring of 4-membered, 5-membered, 6-membered or 7-membered, comprising 1-2 heteroatoms such as nitrogen, oxygen and/or sulphur, and may have one or more (preferably 1-3) suitable substituted group such as, halogen, nitrile group, amino, $C_1$-$C_6$ alkyl, $C_1$-$C_6$ alkoxy, mono-(or bi- or tri-) halogenated (lower) alkyl, etc.

The heterocyclic ring or heteroaryl ring "comprising nitrogen", refers to a ring comprising at least one nitrogen.

Besides, if the present invention relates to percentage between liquid and liquid, the percentage is volume/volume percent; if the present invention relates to percentage between liquid and solid, the percentage is volume/weight percent; if the present invention relates to percentage between solid and liquid, the percentage is weight/volume percent. The others are weight/weight percent.

The oxadiazole compounds of the present invention have excellent anti coxsackie-viruses activity, less toxicity and higher safety, comparing with the prior art.

DETAILED DESCRIPTION OF THE PRESENT INVENTION AND PREFERRED EMBODIMENTS THEREOF

Figure 1A:
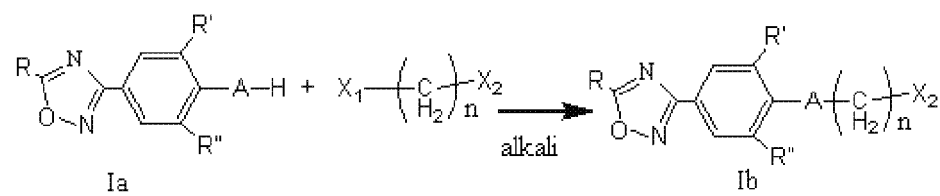
FIG. 1a and FIG. 1b show the flow chart of the preparation method of the oxadiazole compound or pharmaceutically acceptable salt or pharmaceutically acceptable ester as shown in Formula (I) of the present invention.
Figure 1B:
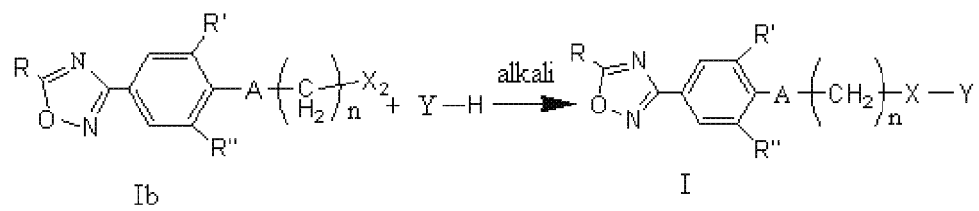
Figure 2:
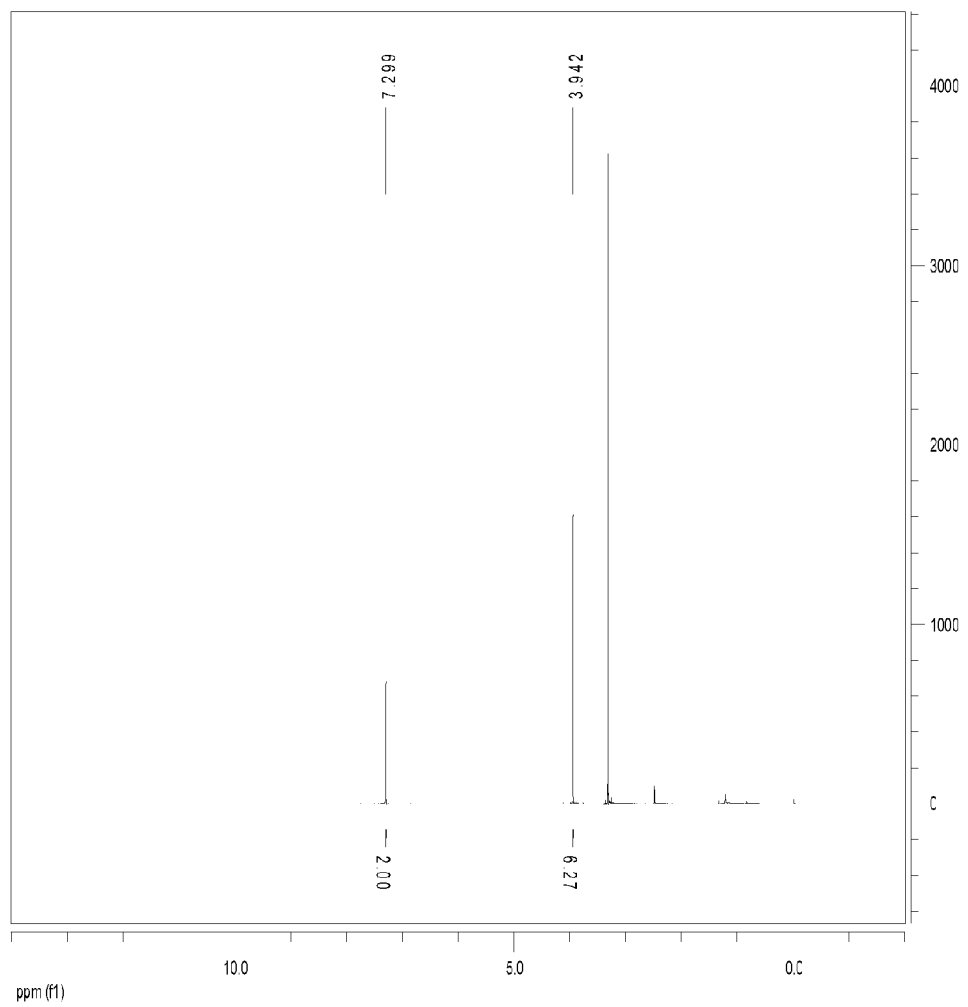
FIG. 2 shows $^1$HNMR spectrogram of compound Ia$_1$ of the present invention.
Figure 3:
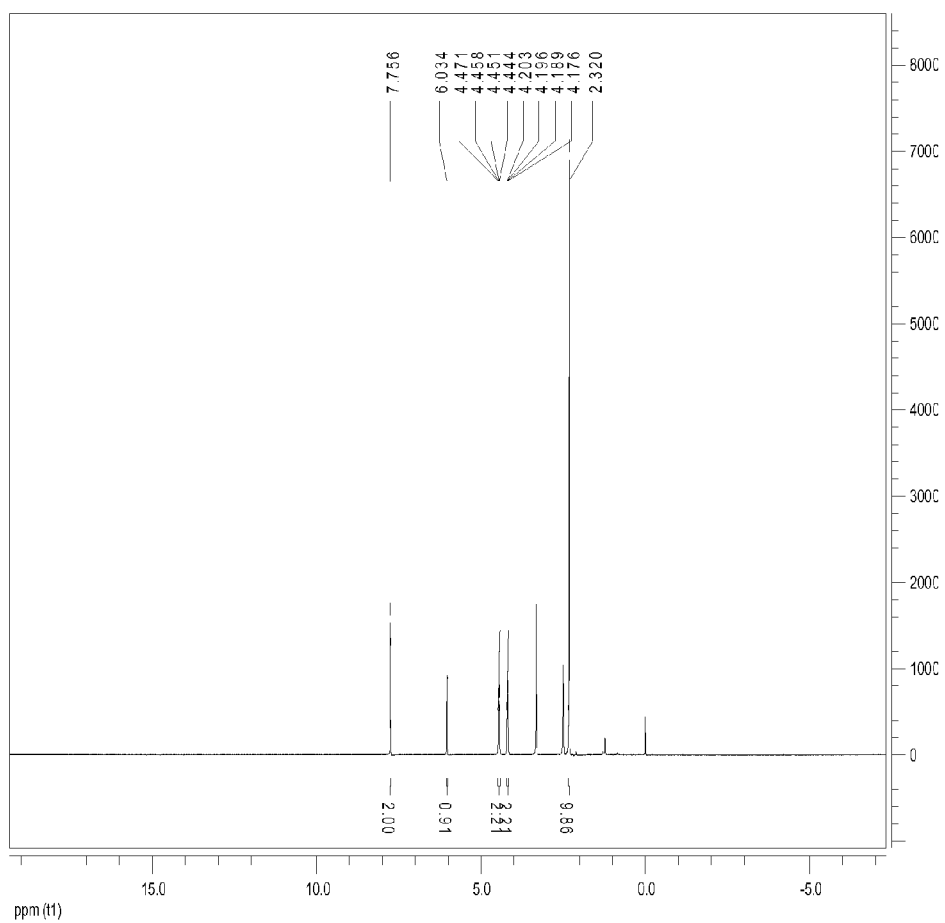
FIG. 3 shows $^1$HNMR spectrogram of compound 1 of the present invention.
Figure 4:
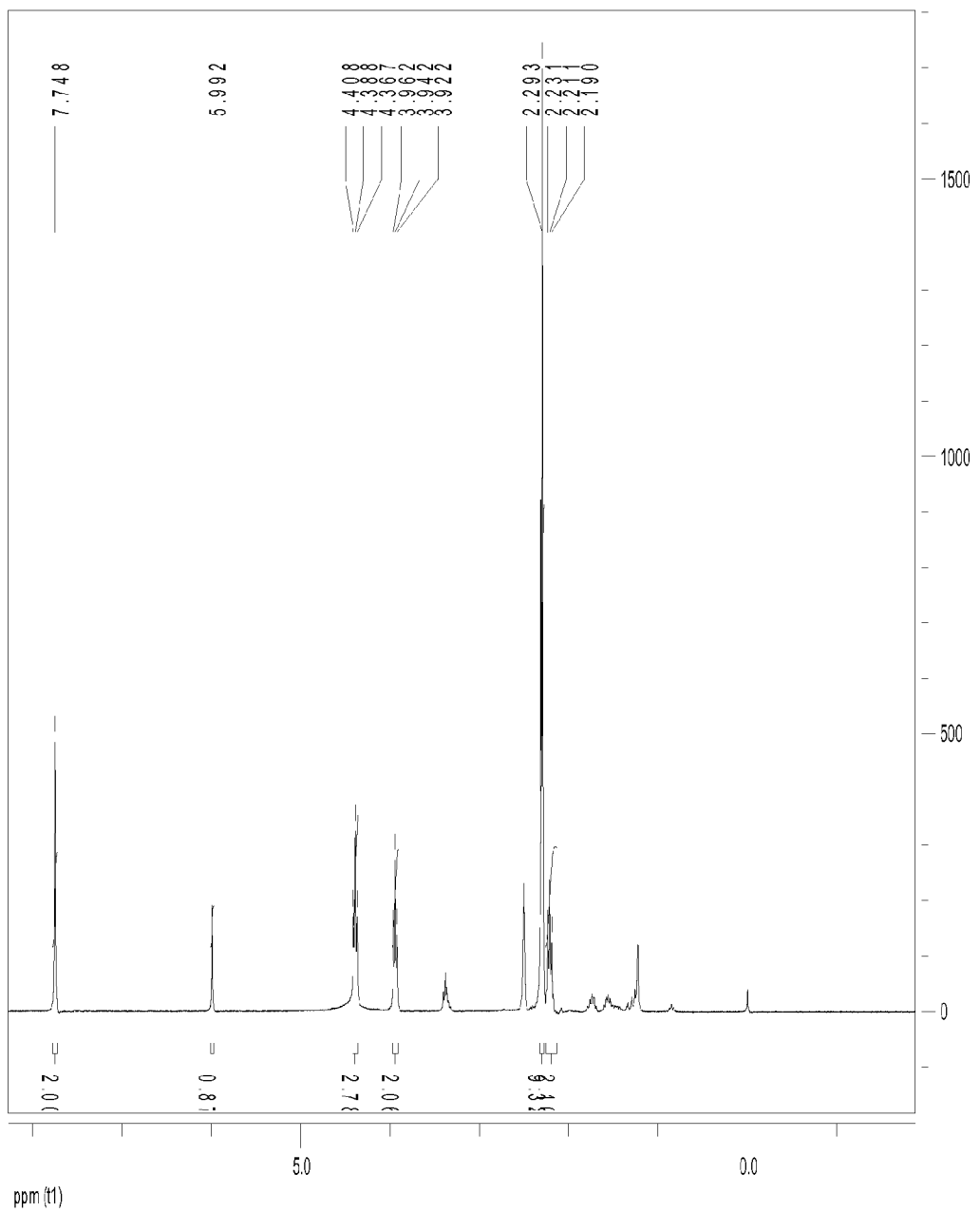
FIG. 4 shows $^1$HNMR spectrogram of compound 6 of the present invention.
Figure 5:
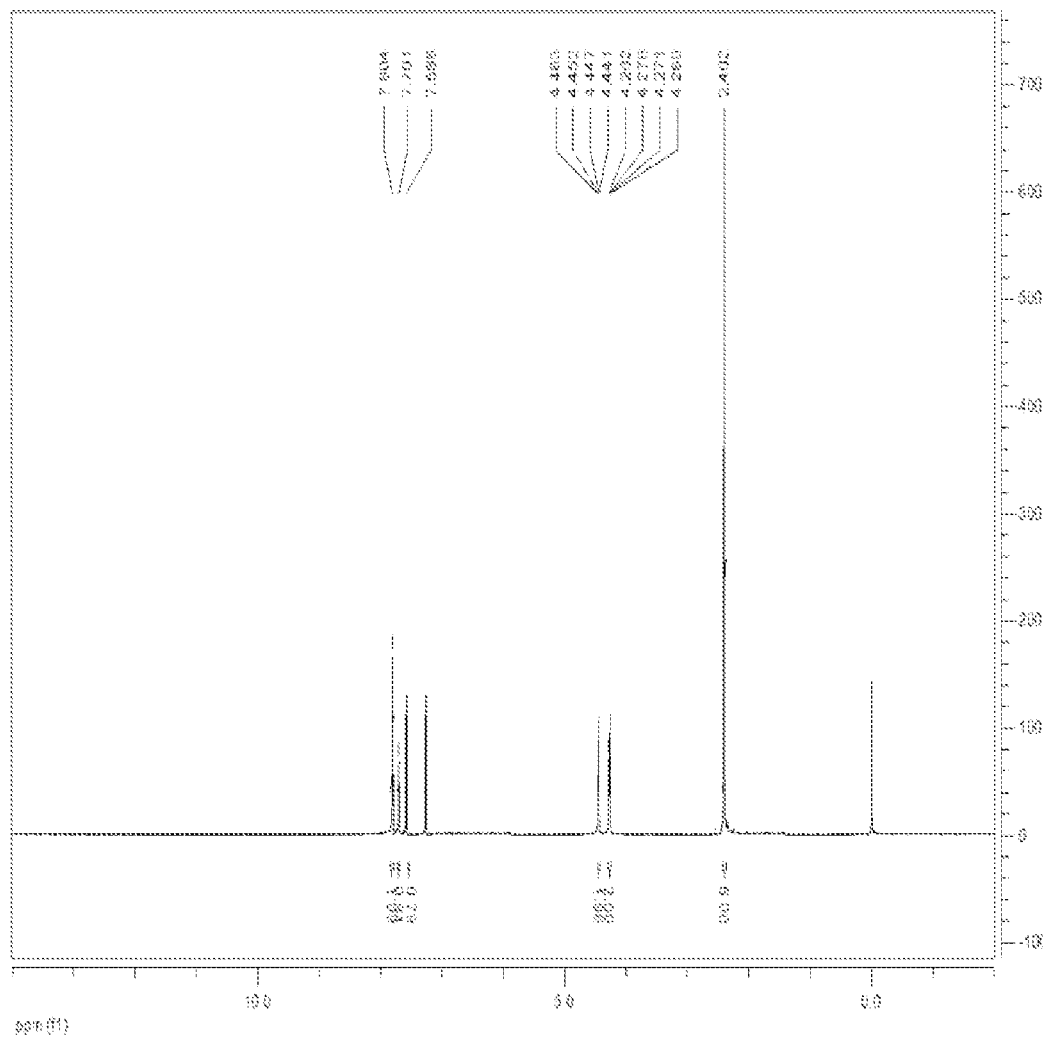
FIG. 5 shows $^1$HNMR spectrogram of compound 46 of the present invention.
Figure 6:
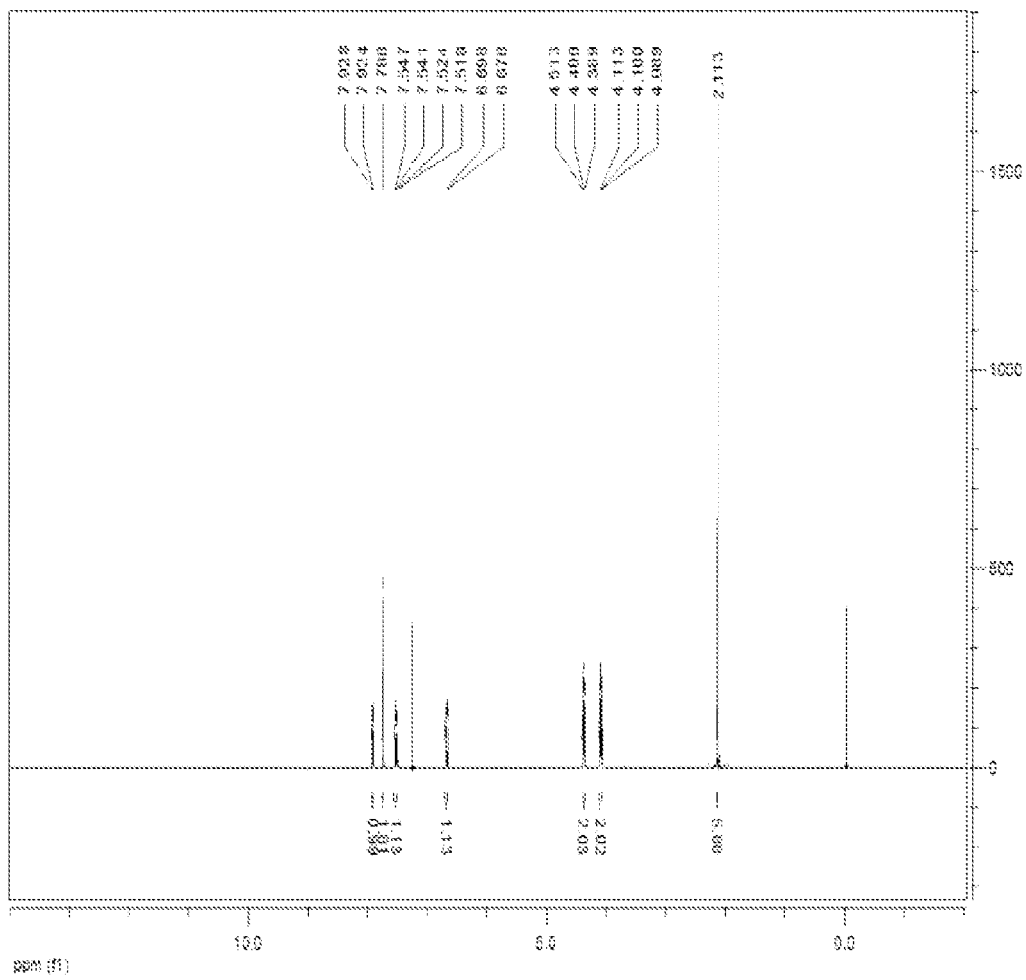
FIG. 6 shows $^1$HNMR spectrogram of compound 50 of the present invention.

Hereafter, the present invention will be described specifically with reference to examples. The examples are given only for illustration of the technical solution of the present invention and should not be construed to limit the present invention.

EXAMPLE 1

Synthesis of Intermediate Ia$_1$ of the Present Invention

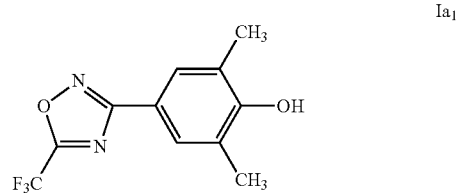 [SMILES: Cc1cc(-c2noc(C(F)(F)F)n2)cc(C)c1O]

50 g of 3,5-dimethyl-4-hydroxybenzonitrile and 47 g of hydroxylamine hydrochloride are added into 1000 ml of ethanol, and heat it to reflux for 4 hours, and detect by thin layer chromatography to confirm whether 3,5-dimethyl-4-hydroxybenzonitrile reacts completely, and then remove ethanol by distillation, 1000 ml of tetrahydrofuran is added, and 286 g of trifluoroacetic anhydride is added slowly, and then heat it to reflux for 4 hours, and filtrate to obtain 30 g of compound $Ia_1$ of the present invention namely, 2,6-dimethyl-4-(5-trifluoromethyl-1,2,4-oxadiazole-3-yl)-phenol, the compound is solid, after cooling.

$Ia_1$ 的 $^1$HNMR (DMSO, 400 MHz) δ: 3.942 (s, 6H), 7.299 (s, 2H).
$^1$HNMR (DMSO, 400 MHz) of $Ia_1$ δ: 3.942 (s, 6H), 7.299 (s, 2H)

EXAMPLE 2

Synthesis of the Intermediate $Ia_2$ 2,6-dimethyl-4-(5-methyl-1,2,4-oxadiazole-3-yl)-phenol of the present invention 27 g of intermediate $Ia_2$, namely, 2,6-dimethyl-4-(5-methyl-1,2,4-oxadiazole-3-yl)-phenol is prepared by using the preparation method of Example 1, wherein acetic anhydride replaces trifluoroacetic anhydride.

$Ia_2$ 的 $^1$HNMR (DMSO, 400 MHz) δ: 3.942 (s, 6H), 3.845 (s, 3H), 7.299 (s, 2H).
$^1$HNMR (DMSO, 400 MHz) of $Ia_2$ δ: 3.942 (s, 6H), 3.845 (s, 3H), 7.299 (s, 2H).

EXAMPLE 3

Synthesis of Compound 1 of the Present Invention 20 g of compound $Ia_1$, 102 g of 1,2-dibromoethane and 5.6 g (40.8 mmol) of potassium carbonate are added into 500 ml of acetonitrile, and heat it to reflux overnight, and then cool it to room temperature, and filtrate it and then wash the filtrate cake by methanol, and then concentrate the filtrate to obtain 22 g white solid compound of 3-[3,5-dimethyl-4-(2-bromoethoxyl)phenyl]-5-(trifluoromethyl)-1,2,4-oxadiazole.

5 g of 3-[3,5-dimethyl-4-(2-bromoethoxy)phenyl]-5-(trifluoromethyl)-1,2,4-oxadiazole, 2.3 g of 3-hydroxy-5-methylisoxazole and 5.5 g of potassium carbonate are added into 100 ml acetonitrile, and then heat it to reflux, and detect by thin layer chromatography to confirm whether the raw material disappears, and cool it to room temperature, and then filtrate and, concentrate the filtrate to obtain 4.9 g of white solid compound 1 of 3-[3,5-dimethyl-4-[2-(5-methylisoxazole-3-oxy)ethoxyl]phenyl]-5-(trifluoromethyl)-1,2,4-oxadiazole of the present invention.

$^1$HNMR (DMSO, 400 MHz) δ: 2.320 (s, 9H), 4.176-4.203 (t, 2H), 4.444-4.474 (t, 2H), 6.034 (s, 1H), 7.756 (s, 2H).

$^1$HNMR (DMSO, 400 MHz) δ: 2.320 (s, 9H), 4.176-4.203 (t, 2H), 4.444-4.474 (t, 2H), 6.034 (s, 1H), 7.756 (s, 2H).

EXAMPLE 4

Synthesis of Compound 2 of the Present Invention 20 g of compound $Ia_2$, 102 g of 1,2-dibromoethane, and 5.6 g (40.8 mmol) of potassium carbonate are added into 500 ml of acetonitrile, and then heat it to reflux overnight, and cool it to room temperature, and then filtrate and wash the filtrate cake by methanol, and concentrate the filtrate to obtain 22 g of white solid compound of 3-[3,5-dimethyl-4-(2-bromoethoxy)phenyl]-5-methyl-1,2,4-oxadiazole.

5 g of 3-[3,5-dimethyl-4-(2-bromoethoxy)phenyl]-5-methyl-1,2,4-oxadiazole, 2.3 g of 3-hydroxy-5-methyl isoxazole and 5.5 g of potassium carbonate are added into 100 ml of acetonitrile, and then heat it to reflux, and detect by thin layer chromatography to confirm whether the raw material disappears, and then cool it to room temperature. filtrate, and concentrate the filtrate to obtain 4.9 g of white solid compound 2 of 3-[3,5-dimethyl-4-[2-(5-methyl isoxazole-3-oxy)ethoxyl]phenyl]-5-methyl-1,2,4-oxadiazole (2) of the present invention.

$^1$HNMR (DMSO, 400 MHz) δ: 2.320 (s, 12H), 3.845 (s, 3H), 4.176-4.203 (t, 2H), 4.444-4.474 (t, 2H), 6.034 (s, 1H), 7.756 (s, 2H).

$^1$HNMR (DMSO, 400 MHz) δ: 2.320 (s, 12H), 3.845 (s, 3H), 4.176-4.203 (t, 2H), 4.444-4.474 (t, 2H), 6.034 (s, 1H), 7.756 (s, 2H).

EXAMPLE 5-139

Synthesis of Compounds 3-137 of the Present Invention

Compounds 3-137 of the present invention are prepared according to the method of Example 3, the structure data and $^1$HNMR (CDCl$_3$, 400 MHz) δ thereof are listed in Table 1.

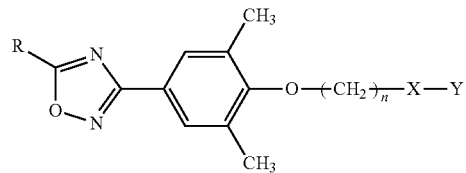

TABLE 1

| Compound | R | n | X | Y | $^1$HNMR (CDCL$_3$, 400 MHz) δ |
|---|---|---|---|---|---|
| 3 | CF$_3$ | 2 | O | (5-trifluoromethyl-isoxazol-3-yl, N—O) | 2.350 (s, 6H), 4.340-4.360 (t, 4H), 5.530 (s, 1H), 6.587 (s, 2H) |
| 4 | CF$_3$ | 2 | O | (N—O isoxazole with COOCH$_3$) | 2.350 (s, 6H), 3.854 (s, 3H), 4.340-4.360 (t, 4H), 6.530 (s, 1H), 6.587 (s, 2H) |
| 5 | CF$_3$ | 2 | O | (O—N isoxazole with CF$_3$) | 2.350 (s, 6H), 4.340-4.360 (t, 4H), 5.730 (s, 1H), 6.587 (s, 2H) |

TABLE 1-continued
| Compound | R | n | X | Y | ¹HNMR (CDCL₃, 400 MHz) δ |
|---|---|---|---|---|---|
| 6 | CF₃ | 3 | O | 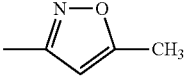 | 2.350 (s, 6H), 2.462-2.520 (m, 2H), 2.784 (s, 3H), 4.240-4.260 (t, 4H), 5.830 (s, 1H), 6.587 (s, 2H) |
| 7 | CF₃ | 3 | O | 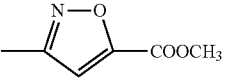 | 2.350 (s, 6H), 2.462-2.520 (m, 2H), 3.984 (s, 3H), 4.240-4.260 (t, 4H), 5.830 (s, 1H), 6.587 (s, 2H) |
| 8 | CF₃ | 3 | O | 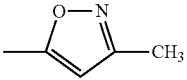 | 2.350 (s, 6H), 2.462-2.520 (m, 2H), 2.784 (s, 3H), 4.240-4.260 (t, 4H), 5.830 (s, 1H), 6.587 (s, 2H) |
| 9 | CF₃ | 3 | O | 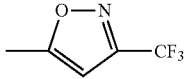 | 2.350 (s, 6H), 2.462-2.520 (m, 2H), 4.240-4.260 (t, 4H), 5.830 (s, 1H), 6.587 (s, 2H) |
| 10 | CF₃ | 2 | O | 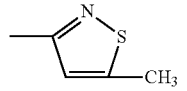 | 2.350 (s, 6H), 2.462 (s, 3H), 4.340-4.360 (t, 4H), 6.430 (s, 1H), 6.587 (s, 2H) |
| 11 | CF₃ | 3 | O | 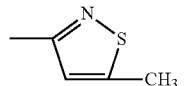 | 2.350 (s, 6H), 2.462 (s, 3H), 2.562-2.620 (m, 2H), 4.240-4.260 (t, 4H), 6.430 (s, 1H), 6.587 (s, 2H) |
| 12 | CF₃ | 2 | O | 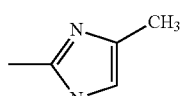 | 2.350 (s, 6H), 2.275 (s, 3H), 4.340-4.360 (t, 4H), .587 (s, 2H), 6.805 (s, 1H), 9.957 (s, 1H) |
| 13 | CF₃ | 2 | O | 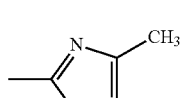 | 2.350 (s, 6H), 2.475 (s, 3H), 4.340-4.360 (t, 4H), 6.155 (s, 1H), 6.587 (s, 2H) |
| 14 | CF₃ | 2 | S | 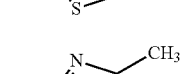 | 2.350 (s, 6H), 2.475 (s, 3H), 3.35-3.45 (t, 2H), 4.340-4.360 (t, 2H), 6.155 (s, 1H), 6.587 (s, 2H) |
| 15 | CF₃ | 2 | O | 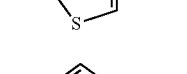 | 2.350 (s, 6H), 2.462 (s, 3H), 4.340-4.360 (t, 4H), 6.430 (s, 1H), 6.587 (s, 2H), 11.623 (s, 1H) |
| 16 | CF₃ | 2 | O | 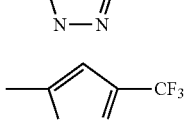 | 2.350 (s, 6H) 3.462 (s, 3H) 4.340-4.360 (t, 4H), 6.430 (s, 1H), 6.587 (s, 2H) |
| 17 | CF₃ | 2 | O | 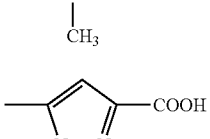 | 2.350 (s, 6H), 3.462 (s, 3H), 4.340-4.360 (t, 4H), 6.430 (s, 1H), .587 (s, 2H) |
| 18 | CF₃ | 2 | S | 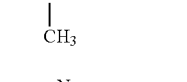 | 2.350 (s, 6H), 2.462 (s, 3H), 4.340-4.360 (t, 4H), 6.430 (s, 1H), 6.587 (s, 2H), 12.054 (s, 1H) |
| 19 | CF₃ | 2 | O | 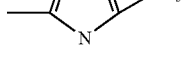 | 2.350 (s, 6H), 2.462 (s, 3H), 4.340-4.360 (t, 4H), 6. 6.587 (s, 2H) |

TABLE 1-continued
| Compound | R | n | X | Y | ¹HNMR (CDCL₃, 400 MHz) δ |
|---|---|---|---|---|---|
| 20 | CF₃ | 3 | O | 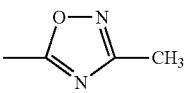 | 2.350 (s, 6H), 2.462 (s, 3H), 2.664-2.670 (m, 2H) 4.240-4.260 (t, 4H), 6. 6.587 (s, 2H) |
| 21 | CF₃ | 2 | O | 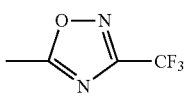 | 2.350 (s, 6H), 4.340-4.360 (t, 4H), 6.587 (s, 2H) |
| 22 | CF₃ | 2 | O | 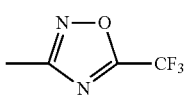 | 2.350 (s, 6H), 4.340-4.360 (t, 4H), 6.587 (s, 2H) |
| 23 | CF₃ | 2 | S | 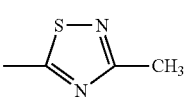 | 2.350 (s, 6H), 2.462 (s, 3H), 3.864-3.870 (m, 2H), 4.240-4.260 (t, 2H), 6. 6.587 (s, 2H) |
| 24 | CF₃ | 2 | O | 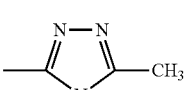 | 2.350 (s, 6H), 2.462 (s, 3H), 4.340-4.360 (t, 4H), 6. 6.587 (s, 2H) |
| 25 | CF₃ | 2 | S | 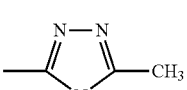 | 2.350 (s, 6H), 2.462 (s, 3H), 3.864-3.870 (m, 2H), 4.240-4.260 (t, 2H), 6. 6.587 (s, 2H) |
| 26 | CF₃ | 2 | S | 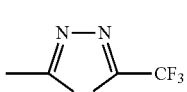 | 2.350 (s, 6H), 3.864-3.870 (m, 2H), 4.240-4.260 (t, 2H), 6. 6.587 (s, 2H) |
| 27 | CF₃ | 2 | S | 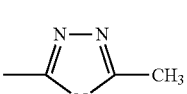 | 2.350 (s, 6H), 2.684 (s, 3H), 3.438 (s, 3H), 3.864-3.870 (m, 2H), 4.240-4.260 (t, 2H), 6. 6.587 (s, 2H) |
| 28 | CF₃ | 2 | O | 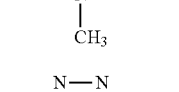 | 2.350 (s, 6H), 2.684 (s, 3H), 4.340-4.360 (t, 4H), 6. 6.587 (s, 2H) |
| 29 | CF₃ | 3 | S | 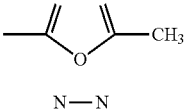 | 2.112-2.204 (m, 2H), 2.350 (s, 6H), 2.684 (s, 3H), 3.456-3.468 (t, 2H), 4.340-4.360 (t, 2H), 6. 6.587 (s, 2H) |
| 30 | CF₃ | 2 | O | 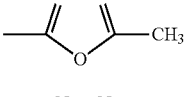 | 2.350 (s, 6H), 4.340-4.360 (t, 4H), 6. 6.587 (s, 2H) |
| 31 | CF₃ | 2 | O | 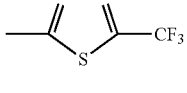 | 2.350 (s, 6H), 4.340-4.360 (t, 4H), 6. 6.587 (s, 2H) |
| 32 | CF₃ | 2 | O | 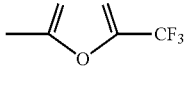 | 2.350 (s, 6H), 4.340-4.360 (t, 4H), 6.587 (s, 2H), 8.492 (s, 1H) |
| 33 | CF₃ | 2 | O | 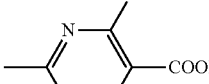 | 2.350 (s, 6H), 4.340-4.360 (t, 4H), 6.324-6.402 (d, H) 6.587 (s, 2H), 8.492-8.510 (d, 1H) |

TABLE 1-continued

| Compound | R | n | X | Y | ¹HNMR (CDCL₃, 400 MHz) δ |
|---|---|---|---|---|---|
| 34 | CF₃ | 2 | S | 2-methyl-4-(trifluoromethyl)pyrimidin-yl | 2.350 (s, 6H), 3.845-3.864 (t, 2H), 4.240-4.260 (t, 2H), 6.324-6.402 (d, H) 6.587 (s, 2H), 8.492-8.510 (d, 1H) |
| 35 | CF₃ | 2 | O | 4-tert-butylcyclohexyl | 1.160 (s, 9H), 2.350 (s, 6H), 4.340-4.360 (t, 4H), 6.587 (s, 2H) |
| 36 | CF₃ | 2 | O | —C—(CH₃)₃ | 2.350 (s, 6H), 4.340-4.360 (t, 4H), 6.587 (s, 2H) |
| 37 | CF₃ | 3 | O | adamantyl | 1.180-1.678 (m, 15H), 1.887-1.894 (m, 2H), 2.350 (s, 6H), 462-2.520 (m, 2H), 4.240-4.260 (t, 4H), 6.587 (s, 2H) |
| 38 | CF₃ | 2 | O | 4-cyano-2-fluorophenyl | 2.350 (s, 6H), 4.340-4.360 (t, 4H), 6.587 (s, 2H) 6.934-6.942 (d, 1H), 7.114 (s, 1H), 7.182-7.186 (d, 1H) |
| 39 | CF₃ | 2 | O | 2-fluoro-4-methylphenyl | 2.350 (s, 9H), 4.340-4.360 (t, 4H), 6.587 (s, 2H), 6.614 (s, 1H), 6.634-6.642 (d, 1H), 6.982-6.986 (d, 1H) |
| 40 | CF₃ | 2 | O | 2-fluoro-4-methoxyphenyl | 2.350 (s, 6H), 3.734 (s, 3H), 4.340-4.360 (t, 4H), 6.374 (s, 1H), 6.634-6.642 (d, 1H), 6.482-6.486 (d, 1H), 6.587 (s, 2H) |
| 41 | CF₃ | 2 | O | 2-fluoro-4-nitrophenyl | 2.350 (s, 6H), 4.340-4.360 (t, 4H), 6.374 (s, 1H), 6.634-6.642 (d, 1H), 6.482-6.486 (d, 1H), 6.587 (s, 2H) |
| 42 | CF₃ | 2 | O | 2,6-dichlorophenyl | 2.350 (s, 6H), 4.340-4.360 (t, 4H), 6.582-6.586 (t, 1H), 6.587 (s, 2H), 7.087-7.092 (d, 2H) |
| 43 | CF₃ | 2 | O | 2,4-dichlorophenyl | 2.350 (s, 6H), 4.340-4.360 (t, 4H), 6.582-6.586 (d, 1H), 6.587 (s, 2H), 7.087-7.092 (d, 1H), 7.187-7.192 (d, 1H) |
| 44 | CF₃ | 2 | O | 5-(((ethoxyimino)methyl)pyridin-2-yl | 1.112-1.124 (t, 3H), 2.350 (s, 6H), 3.578-3.584 (m, 2H), 4.340-4.360 (t, 4H), 6.587 (s, 2H), 7.587-7.592 (s, 1H), 7.687-7.692 (d, 1H), 7.987-7.992 (d, 1H), 8.724 (s, 1H) |
| 45 | CF₃ | 2 | O | 6-(((ethoxyimino)methyl)pyridin-3-yl | 1.112-1.124 (t, 3H), 2.350 (s, 6H), 3.578-3.584 (m, 2H), 4.340-4.360 (t, 4H), 6.587 (s, 2H), 6.887-6.892 (d, 1H), 7.502 (s, 1H), 8.081 (s, 1H), 8.182-8.192 (d, 2H) |

TABLE 1-continued

| Compound | R | n | X | Y | ¹HNMR (CDCL₃, 400 MHz) δ |
|---|---|---|---|---|---|
| 46 | CF₃ | 2 | O | 2-methyl-3-fluoro-5-cyanopyridine | 2.350 (s, 6H), 4.340-4.360 (t, 4H), 6.587 (s, 2H), 8.087 (s, 1H), 8.187 (s, 1H) |
| 47 | CF₃ | 2 | O | 2-methyl-3-fluoro-5-methylpyridine | 2.320 (s, 3H), 2.350 (s, 6H), 4.340-4.360 (t, 4H), 6.587 (s, 2H), 7.087 (s, 1H), 7.487 (s, 1H) |
| 48 | CF₃ | 2 | O | 2-hydroxy-3-cyano-5-fluoro-6-methylpyridine | 2.350 (s, 6H), 4.340-4.360 (t, 4H), 6.587 (s, 2H), 8.087 (s, 1H) |
| 49 | CF₃ | 2 | O | 2-methyl-3-fluoro-5-methoxycarbonylpyridine | 2.350 (s, 6H), 3.882 (s, 3H), 4.340-4.360 (t, 4H), 6.587 (s, 2H), 8.067 (s, 1H), 8.087 (s, 1H) |
| 50 | CF₃ | 2 | O | 2-methyl-5-cyanopyridine | 2.350 (s, 6H), 4.340-4.360 (t, 4H), 6.587 (s, 2H), 7.067-7.084 (d, 1H), 8.387 (s, 1H), 8.472-8.480 (d, 1H) |
| 51 | CF₃ | 2 | O | 2-methyl-5-methylpyridine | 2.320 (s, 3H), 2.350 (s, 6H), 4.340-4.360 (t, 4H), 6.587 (s, 2H), 6.967-6.984 (d, 1H), 7.687 (s, 1H), 7.772-7.780 (d, 1H) |
| 52 | CF₃ | 2 | O | 2-methyl-5-trifluoromethylpyridine | 2.350 (s, 6H), 4.340-4.360 (t, 4H), 6.587 (s, 2H), 6.767-6.784 (d, 1H), 7.787 (s, 1H), 7.872-7.880 (d, 1H) |
| 53 | CF₃ | 2 | O | 2-hydroxy-5-fluoro-4-methylpyrimidine | 2.350 (s, 6H), 4.340-4.360 (t, 4H), 6.587 (s, 2H), 8.372 (s, 1H) |
| 54 | CF₃ | 2 | O | 2-methoxy-5-fluoro-4-methylpyrimidine | 2.350 (s, 6H), 3.730 (s, 3H), 4.340-4.360 (t, 4H), 6.587 (s, 2H), 8.272 (s, 1H) |
| 55 | CF₃ | 2 | O | 3-methyl-2-carbamoyl-5-fluoropyrazine | 2.350 (s, 6H), 4.340-4.360 (t, 4H), 6.587 (s, 2H), 8.292 (s, 1H), 9.290-9.332 (m, 2H) |
| 56 | CF₃ | 2 | O | 3,6-dimethylpyridazine | 2.350 (s, 9H), 4.340-4.360 (t, 4H), 6.587 (s, 2H), 6.872-6.892 (d, 1H), 7.290-7.332 (d, 1H) |

TABLE 1-continued

| Compound | R | n | X | Y | $^1$HNMR (CDCL$_3$, 400 MHz) δ |
|---|---|---|---|---|---|
| 57 | CH$_3$ | 2 | O | 3-methyl-5-CF$_3$-isoxazol-yl (N—O, CF$_3$ at 5) | 2.350 (s, 9H), 4.340-4.360 (t, 4H), 5.530 (s, 1H), 6.587 (s, 2H) |
| 58 | CH$_3$ | 2 | O | 3-methyl-5-COOCH$_3$-isoxazol-yl | 2.350 (s, 9H), 3.854 (s, 3H), 4.340-4.360 (t, 4H), 6.530 (s, 1H), 6.587 (s, 2H) |
| 59 | CH$_3$ | 2 | O | 5-methyl-3-CF$_3$-isoxazol-yl (O—N) | 2.350 (s, 9H), 4.340-4.360 (t, 4H), 5.730 (s, 1H), 6.587 (s, 2H) |
| 60 | CH$_3$ | 3 | O | 3-methyl-5-CH$_3$-isoxazol-yl (N—O) | 2.350 (s, 9H), 2.462-2.520 (m, 2H), 2.784 (s, 3H), 4.240-4.260 (t, 4H), 5.830 (s, 1H), 6.587 (s, 2H) |
| 61 | CH$_3$ | 3 | O | 3-methyl-5-COOCH$_3$-isoxazol-yl | 2.350 (s, 9H), 2.462-2.520 (m, 2H), 3.984 (s, 3H), 4.240-4.260 (t, 4H), 5.830 (s, 1H), 6.587 (s, 2H) |
| 62 | CH$_3$ | 3 | O | 5-methyl-3-CH$_3$-isoxazol-yl (O—N) | 2.350 (s, 9H), 2.462-2.520 (m, 2H), 2.784 (s, 3H), 4.240-4.260 (t, 4H), 5.830 (s, 1H), 6.587 (s, 2H) |
| 63 | CH$_3$ | 3 | O | 5-methyl-3-CF$_3$-isoxazol-yl (O—N) | 2.350 (s, 9H), 2.462-2.520 (m, 2H), 4.240-4.260 (t, 4H), 5.830 (s, 1H), 6.587 (s, 2H) |
| 64 | CH$_3$ | 2 | O | 3,5-dimethyl-isothiazol-yl | 2.350 (s, 9H), 2.462 (s, 3H), 4.340-4.360 (t, 4H), 6.430 (s, 1H), 6.587 (s, 2H) |
| 65 | CH$_3$ | 3 | O | 3,5-dimethyl-isothiazol-yl | 2.350 (s, 9H), 2.462 (s, 3H), 2.562-2.620 (m, 2H), 4.240-4.260 (t, 4H), 6.430 (s, 1H), 6.587 (s, 2H) |
| 66 | CH$_3$ | 2 | O | 2-methyl-4-methyl-imidazol-yl | 2.350 (s, 9H), 2.275 (s, 3H), 4.340-4.360 (t, 4H), 6.587 (s, 2H), 6.805 (s, 1H), 9.957 (s, 1H) |
| 67 | CH$_3$ | 2 | O | 2-methyl-4-methyl-thiazol-yl | 2.350 (s, 9H), 2.475 (s, 3H), 4.340-4.360 (t, 4H), 6.155 (s, 1H), 6.587 (s, 2H) |
| 68 | CH$_3$ | 2 | S | 2-methyl-4-methyl-thiazol-yl | 2.350 (s, 9H), 2.475 (s, 3H), 3.35-3.45 (t, 2H), 4.340-4.360 (t, 2H), 6.155 (s, 1H), 6.587 (s, 2H) |
| 69 | CH$_3$ | 2 | O | 3,5-dimethyl-pyrazol-yl | 2.350 (s, 9H), 2.462 (s, 3H), 4.340-4.360 (t, 4H), 6.430 (s, 1H), 6.587 (s, 2H), 11.623 (s, 1H) |
| 70 | CH$_3$ | 2 | O | 5-methyl-3-CF$_3$-1-methyl-pyrazol-yl | 2.350 (s, 9H), 3.462 (s, 3H), 4.340-4.360 (t, 4H), 6.430 (s, 1H), 6.587 (s, 2H) |

TABLE 1-continued

| Compound | R | n | X | Y | ¹HNMR (CDCL₃, 400 MHz) δ |
|---|---|---|---|---|---|
| 71 | CH₃ | 2 | O | 1-methyl-3-COOH-pyrazol-5-yl | 2.350 (s, 9H), 3.462 (s, 3H), 4.340-4.360 (t, 4H), 6.430 (s, 1H), 6.587 (s, 2H) |
| 72 | CH₃ | 2 | O | 4-methyl-imidazol-2-yl | 2.350 (s, 9H), 2.462 (s, 3H), 4.340-4.360 (t, 4H), 6.430 (s, 1H), 6.587 (s, 2H), 12.054 (s, 1H) |
| 73 | CH₃ | 2 | O | 3-methyl-1,2,4-oxadiazol-5-yl | 2.350 (s, 9H), 2.462 (s, 3H), 4.340-4.360 (t, 4H), 6. 6.587 (s, 2H) |
| 74 | CH₃ | 3 | O | 3-methyl-1,2,4-oxadiazol-5-yl | 2.350 (s, 9H), 2.462 (s, 3H), 2.664-2.670 (m, 2H), 4.240-4.260 (t, 4H), 6. 6.587 (s, 2H) |
| 75 | CH₃ | 2 | O | 3-CF₃-1,2,4-oxadiazol-5-yl | 2.350 (s, 9H), 4.340-4.360 (t, 4H), 6.587 (s, 2H) |
| 76 | CH₃ | 2 | O | 5-CF₃-1,2,4-oxadiazol-3-yl | 2.350 (s, 9H), 4.340-4.360 (t, 4H), 6.587 (s, 2H) |
| 77 | CH₃ | 2 | S | 3-methyl-1,2,4-thiadiazol-5-yl | 2.350 (s, 9H), 2.462 (s, 3H), 3.864-3.870 (m, 2H), 4.240-4.260 (t, 2H), 6. 6.587 (s, 2H) |
| 78 | CH₃ | 2 | O | 3-methyl-1,2,4-triazol-5-yl | 2.350 (s, 9H), 2.462 (s, 3H), 4.340-4.360 (t, 4H), 6. 6.587 (s, 2H) |
| 79 | CH₃ | 2 | S | 3-methyl-1,2,4-triazol-5-yl | 2.350 (s, 9H), 2.462 (s, 3H), 3.864-3.870 (m, 2H), 4.240-4.260 (t, 2H), 6. 6.587 (s, 2H) |
| 80 | CH₃ | 2 | S | 3-CF₃-1,2,4-triazol-5-yl | 2.350 (s, 9H), 3.864-3.870 (m, 2H), 4.240-4.260 (t, 2H), 6. 6.587 (s, 2H) |
| 81 | CH₃ | 2 | S | 1,3-dimethyl-1,2,4-triazol-5-yl | 2.350 (s, 9H), 2.684 (s, 3H), 3.438 (s, 3H), 3.864-3.870 (m, 2H), 4.240-4.260 (t, 2H), 6. 6.587 (s, 2H) |
| 82 | CH₃ | 2 | O | 2-methyl-1,3,4-oxadiazol-5-yl | 2.350 (s, 9H), 2.684 (s, 3H), 4.340-4.360 (t, 4H), 6. 6.587 (s, 2H) |
| 83 | CH₃ | 3 | S | 2-methyl-1,3,4-oxadiazol-5-yl | 2.112-2.204 (m, 2H), 2.350 (s, 9H), 2.684 (s, 3H), 3.456-3.468 (t, 2H), 4.340-4.360 (t, 2H), 6. 6.587 (s, 2H) |
| 84 | CH₃ | 2 | O | 2-CF₃-1,3,4-thiadiazol-5-yl | 2.350 (s, 9H), 4.340-4.360 (t, 4H), 6. 6.587 (s, 2H) |

TABLE 1-continued

| Compound | R | n | X | Y | $^1$HNMR (CDCL$_3$, 400 MHz) δ |
|---|---|---|---|---|---|
| 85 | CH$_3$ | 2 | O | 5-methyl-2-(trifluoromethyl)-1,3,4-oxadiazole | 2.350 (s, 9H), 4.340-4.360 (t, 4H), 6.6.587 (s, 2H) |
| 86 | CH$_3$ | 2 | O | 4-hydroxy-2-methylpyrimidine-5-carboxylic acid | 2.350 (s, 9H), 4.340-4.360 (t, 4H), 6.587 (s, 2H), 8.492 (s, 1H) |
| 87 | CH$_3$ | 2 | O | 2-methyl-4-(trifluoromethyl)pyrimidine | 2.350 (s, 9H), 4.340-4.360 (t, 4H), 6.324-6.402 (d, H) 6.587 (s, 2H), 8.492-8.510 (d, 1H) |
| 88 | CH$_3$ | 2 | S | 2-methyl-4-(trifluoromethyl)pyrimidine | 2.350 (s, 9H), 3.845-3.864 (t, 2H), 4.240-4.260 (t, 2H), 6.324-6.402 (d, H) 6.587 (s, 2H), 8.492-8.510 (d, 1H) |
| 89 | CH$_3$ | 2 | O | methylcyclohexane | 1.160 (s, 9H), 2.350 (s, 9H), 4.340-4.360 (t, 4H), 6.587 (s, 2H) |
| 90 | CH$_3$ | 2 | O | —C—(CH$_3$)$_3$ | 2.350 (s, 9H), 4.340-4.360 (t, 4H), 6.587 (s, 2H) |
| 91 | CH$_3$ | 3 | O | adamantyl | 1.180-1.678 (m, 15H), 1.887-1.894 (m, 2H), 2.350 (s, 9H), 2.462-2.520 (m, 2H), 4.240-4.260 (t, 4H), 6.587 (s, 2H) |
| 92 | CH$_3$ | 2 | O | 3-fluoro-4-methylbenzonitrile | 2.350 (s, 9H), 4.340-4.360 (t, 4H), 6.587 (s, 2H) 6.934-6.942 (d, 1H), 7.114 (s, 1H), 7.182-7.186 (d, 1H) |
| 93 | CH$_3$ | 2 | O | 3-fluoro-4-methyl-methylbenzene | 2.350 (s, 12H), 4.340-4.360 (t, 4H), 6.587 (s, 2H), 6.614 (s, 1H), 6.634-6.642 (d, 1H), 6.982-6.986 (d, 1H) |
| 94 | CH$_3$ | 2 | O | 3-fluoro-4-methyl-methoxybenzene | 2.350 (s, 9H), 3.734 (s, 3H), 4.340-4.360 (t, 4H), 6.374 (s, 1H), 6.634-6.642 (d, 1H), 6.482-6.486 (d, 1H), 6.587 (s, 2H) |
| 95 | CH$_3$ | 2 | O | 3-fluoro-4-methyl-nitrobenzene | 2.350 (s, 9H), 4.340-4.360 (t, 4H), 6.374 (s, 1H), 6.634-6.642 (d, 1H), 6.482-6.486 (d, 1H), 6.587 (s, 2H) |
| 96 | CH$_3$ | 2 | O | 2,6-dichloro-methylbenzene | 2.350 (s, 9H), 4.340-4.360 (t, 4H), 6.582-6.586 (t, 1H), 6.587 (s, 2H), 7.087-7.092 (d, 2H) |

TABLE 1-continued

| Compound | R | n | X | Y | ¹HNMR (CDCL₃, 400 MHz) δ |
|---|---|---|---|---|---|
| 97 | CH₃ | 2 | O | 2,5-dichloro-4-methylphenyl | 2.350 (s, 9H), 4.340-4.360 (t, 4H), 6.582-6.586 (d, 1H), 6.587 (s, 2H), 7.087-7.092 (d, 1H), 7.187-7.192 (d, 1H) |
| 98 | CH₃ | 2 | O | 5-methylpyridin-2-yl CH=N—OC₂H₅ | 1.112-1.124 (t, 3H), 2.350 (s, 9H), 3.578-3.584 (m, 2H), 4.340-4.360 (t, 4H), 6.587 (s, 2H), 7.587-7.592 (s, 1H), 7.687-7.692 (d, 1H), 7.987-7.992 (d, 1H), 8.724 (s, 1H) |
| 99 | CH₃ | 2 | O | 6-methylpyridin-3-yl CH=N—OC₂H₅ | 1.112-1.124 (t, 3H), 2.350 (s, 9H), 3.578-3.584 (m, 2H), 4.340-4.360 (t, 4H), 6.587 (s, 2H), 6.887-6.892 (d, 1H), 7.502 (s, 1H), 8.081 (s, 1H), 8.182-8.192 (d, 2H) |
| 100 | CH₃ | 2 | O | 5-fluoro-6-methyl-pyridin-3-yl CN | 2.350 (s, 9H), 4.340-4.360 (t, 4H), 6.587 (s, 2H), 8.087 (s, 1H), 8.187 (s, 1H) |
| 101 | CH₃ | 2 | O | 3-fluoro-2-methyl-5-methylpyridine | 2.320 (s, 3H), 2.350 (s, 9H), 4.340-4.360 (t, 4H), 6.587 (s, 2H), 7.087 (s, 1H), 7.487 (s, 1H) |
| 102 | CH₃ | 2 | O | 2-hydroxy-3-cyano-5-fluoro-6-methylpyridine | 2.350 (s, 9H), 4.340-4.360 (t, 4H), 6.587 (s, 2H), 8.087 (s, 1H) |
| 103 | CH₃ | 2 | O | 5-fluoro-6-methyl-pyridin-3-yl COOCH₃ | 2.350 (s, 9H), 3.882 (s, 3H), 4.340-4.360 (t, 4H), 6.587 (s, 2H), 8.067 (s, 1H), 8.087 (s, 1H) |
| 104 | CH₃ | 2 | O | 6-methylpyridin-3-yl CN | 2.350 (s, 9H), 4.340-4.360 (t, 4H), 6.587 (s, 2H), 7.067-7.084 (d, 1H), 8.387 (s, 1H), 8.472-8.480 (d, 1H) |
| 105 | CH₃ | 2 | O | 6-methyl-5-methylpyridin-2-yl | 2.320 (s, 3H), 2.350 (s, 9H), 4.340-4.360 (t, 4H), 6.587 (s, 2H), 6.967-6.984 (d, 1H), 7.687 (s, 1H), 7.772-7.780 (d, 1H) |
| 106 | CH₃ | 2 | O | 6-methyl-5-trifluoromethylpyridin-2-yl | 2.350 (s, 9H), 4.340-4.360 (t, 4H), 6.587 (s, 2H), 6.767-6.784 (d, 1H), 7.787 (s, 1H), 7.872-7.880 (d, 1H) |
| 107 | CH₃ | 2 | O | 2-hydroxy-5-fluoro-6-methylpyrimidine | 2.350 (s, 9H), 4.340-4.360 (t, 4H), 6.587 (s, 2H), 8.372 (s, 1H) |

TABLE 1-continued

| Compound | R | n | X | Y | ¹HNMR (CDCL₃, 400 MHz) δ |
|---|---|---|---|---|---|
| 108 | CH₃ | 2 | O | 5-fluoro-4-methyl-2-methoxypyrimidine | 2.350 (s, 9H), 3.730 (s, 3H), 4.340-4.360 (t, 4H), 6.587 (s, 2H), 8.272 (s, 1H) |
| 109 | CH₃ | 2 | O | 5-fluoro-3-methyl-2-carbamoylpyrazine | 2.350 (s, 9H), 4.340-4.360 (t, 4H), 6.587 (s, 2H), 8.292 (s, 1H), 9.290-9.332 (m, 2H) |
| 110 | CH₃ | 2 | O | 3,6-dimethylpyridazine | 2.350 (s, 12H), 4.340-4.360 (t, 4H), 6.587 (s, 2H), 6.872-6.892 (d, 1H), 7.290-7.332 (d, 1H) |
| 111 | CF₃ | 2 | 0 | 3-phenyl-5-methyl-1,2,4-oxadiazole | 2.350 (s, 9H), 4.360-4.380 (t, 4H), 6.830-6.836 (d, 2H), 6.984 (s, 2H), 7.374-7.377 (d, 2H) |
| 112 | CF₃ | 2 | 0 | 3-phenyl-5-trifluoromethyl-1,2,4-oxadiazole | 2.350 (s, 6H), 4.360-4.380 (t, 4H), 6.830-6.836 (d, 2H), 6.984 (s, 2H), 7.374-7.377 (d, 2H) |
| 113 | CF₃ | 2 | 0 | 3-(pyridin-3-yl)-5-methyl-1,2,4-oxadiazole | 2.350 (s, 9H), 4.360-4.380 (t, 4H), 6.730-6.736 (d, 1H), 6.984 (s, 2H), 7.914 (s, 1H), 7.974-7.978 (d, 1H) |
| 114 | CF₃ | 2 | 0 | 3-(pyridin-3-yl)-5-trifluoromethyl-1,2,4-oxadiazole | 2.350 (s, 6H), 4.360-4.380 (t, 4H), 6.730-6.736 (d, 1H), 6.984 (s, 2H), 7.914 (s, 1H), 7.974-7.978 (d, 1H) |
| 115 | CF₃ | 2 | 0 | 3-(5-fluoropyridin-3-yl)-5-methyl-1,2,4-oxadiazole | 2.350 (s, 9H), 4.360-4.380 (t, 4H), 6.730-6.736 (d, 1H), 6.984 (s, 2H), 7.684 (s, 2H) |
| 116 | CF₃ | 2 | 0 | 3-(5-fluoropyridin-3-yl)-5-trifluoromethyl-1,2,4-oxadiazole | 2.350 (s, 6H), 4.360-4.380 (t, 4H), 6.730-6.736 (d, 1H), 6.984 (s, 2H), 7.684 (s, 2H) |
| 117 | CF₃ | 3 | 0 | 3-phenyl-5-methyl-1,2,4-oxadiazole | 2.134-2.140 (m, 2H), 2.350 (s, 9H), 3.960-3.980 (t, 4H), 6.830-6.836 (d, 2H), 6.984 (s, 2H), 7.374-7.377 (d, 2H) |
| 118 | CF₃ | 3 | 0 | 3-phenyl-5-trifluoromethyl-1,2,4-oxadiazole | 2.134-2.140 (m, 2H), 2.350 (s, 6H), 3.960-3.980 (t, 4H) 6.830-6.836 (d 2H) 6.984 (s 2H) 7.374-7.377 (d, 2H) |
| 119 | CF₃ | 3 | 0 | 3-(pyridin-3-yl)-5-methyl-1,2,4-oxadiazole | 2.134-2.140 (m, 2H), 2.350 (s, 9H), 3.960-3.980 (t, 4H), 6.730-6.736 (d, 1H), 6.984 (s, 2H), 7.914 (s, 1H), 7.974-7.978 (d, 1H) |

TABLE 1-continued

| Compound | R | n | X | Y | ¹HNMR (CDCL₃, 400 MHz) δ |
|---|---|---|---|---|---|
| 120 | CF₃ | 3 | 0 | 3-pyridyl-1,2,4-oxadiazole-CF₃ | 2.134-2.140 (m, 2H), 2.350 (s, 6H), 3.960-3.980 (t, 4H), 6.730-6.736 (d, 1H), 6.984 (s, 2H), 7.684 (s, 2H) |
| 121 | CF₃ | 3 | 0 | 5-fluoro-pyridyl-oxadiazole-CH₃ | 2.130-2.138 (m, 2H), 2.350 (s, 9H), 3.960-3.980 (t, 4H), 6.730-6.736 (d, 1H), 6.984 (s, 2H), 7.684 (s, 2H) |
| 122 | CF₃ | 3 | 0 | 5-fluoro-pyridyl-oxadiazole-CF₃ | 2.132-2.139 (m, 2H), 2.350 (s, 6H), 3.960-3.980 (t, 4H), 6.730-6.736 (d, 1H), 6.984 (s, 2H), 7.684 (s, 2H) |
| 123 | CF₃ | 2 | 0 | 3-fluoro-phenyl-oxadiazole-CH₃ | 2.350 (s, 6H), 4.360-4.380 (t, 4H), 6.730-6.736 (d, 1H), 6.984 (s, 2H), 7.084-7.234 (m, 2H) |
| 124 | CF₃ | 3 | 0 | 3-fluoro-phenyl-oxadiazole-CF₃ | 2.132-2.139 (m, 2H), 2.350 (s, 9H), 3.860-3.880 (t, 4H), 6.730-6.736 (d 1H), 6.984 (s, 2H), 7.084-7.234 (m, 2H) |
| 125 | CF₃ | 2 | O | 2-methylthiophene | 2.134-2.140 (m, 2H), 2.350 (s, 6H), 2.421 (s, 3H), 3.960-3.980 (t, 4H), 5.782-5.788 (d, 1H), 6.174-6.180 (d, 1H), 6.984 (s, 2H) |
| 126 | CF₃ | 2 | O | 2-methylfuran | 2.134-2.140 (m, 2H), 2.182 (s, 3H), 2.350 (s, 6H), 3.960-3.980 (t, 4H), 4.782-4.788 (d, 1H), 5.674-5.680 (d, 1H), 6.984 (s, 2H) |
| 127 | CF₃ | 2 | O | 2-methylpyrrole | 2.134-2.140 (m, 2H), 2.162 (s, 3H), 2.350 (s, 6H), 3.960-3.980 (t, 4H), 5.674-5.880 (d, 2H), 6.984 (s, 2H) |
| 128 | CH₃ | 2 | O | 1-methyl-tetrazole | 2.350 (s, 6H), 3.634 (s, 3H), 4.360-4.380 (t, 4H), 6.984 (s, 2H) |
| 129 | CF₃ | 3 | O | 1,2-dimethylcyclohexane | 1.062-1.080 (d, 6H), 1.270-1.451 (m, 4H), 1.601-1.712 (m, 4H), 1.884-1.899 (m, 2H), 2.350 (s, 6H), 2.791-2.802 (m, 1H), 3.960-3.980 (t, 4H) 6.984 (s, 2H) |
| 130 | CF₃ | 3 | O | 3,5-dichloro-methylphenyl | 2.131-2.140 (m, 2H), 2.350 (s, 9H), 3.960-3.980 (t, 4H), 6.841 (s, 2H), 6.984 (s, 2H) |
| 131 | CF₃ | 3 | O | pyrazine-2-CN | 2.131-2.140 (m, 2H), 2.350 (s, 6H), 3.960-3.980 (t, 4H), 6.841 (s, 2H), 8.284 (s, 2H) |

TABLE 1-continued

| Compound | R | n | X | Y | $^1$HNMR (CDCL$_3$, 400 MHz) δ |
|---|---|---|---|---|---|
| 132 | CF$_3$ | 3 | O | pyrazine-CN | 2.131-2.140 (m, 2H), 2.350 (s, 6H), 3.960-3.980 (t, 4H), 6.841 (s, 2H), 9.184 (s, 2H) |
| 133 | CF$_3$ | 3 | O | pyridazine-CN | 2.131-2.140 (m, 2H), 2.350 (s, 6H), 3.960-3.980 (t, 4H), 6.841 (s, 2H), 7.184-7.190 (d, 1H), 8.110-8.121 (d, 2H) |
| 134 | CF$_3$ | 3 | O | pyridine-NO$_2$ | 2.131-2.140 (m, 2H), 2.350 (s, 6H), 3.960-3.980 (t, 4H), 6.841 (s, 2H), 6.941-6.950 (d, 1H), 8.610-8.641 (m, 2H) |
| 135 | CF$_3$ | 3 | O | pyrimidine-oxadiazole-CF$_3$ | 2.131-2.140 (m, 2H), 2.350 (s, 6H), 3.960-3.980 (t, 4H), 6.841 (s, 2H), 8.284 (s, 2H) |
| 136 | CF$_3$ | 3 | O | pyrazine-oxadiazole-CF$_3$ | 2.131-2.140 (m, 2H), 2.350 (s, 6H), 3.960-3.980 (t, 4H), 6.841 (s, 2H), 9.184 (s, 2H) |
| 137 | CF$_3$ | 3 | O | pyridazine-oxadiazole-CF$_3$ | 2.131-2.140 (m, 2H), 2.350 (s, 6H), 3.960-3.980 (t, 4H), 6.841 (s, 2H), 7.184-7.190 (d, 1H), 8.110-8.121 (d, 2H) |

EXAMPLE 140

Experimental Results of Anti-Cox_B$_3$ of the Compounds 1-137 of the Present Invention The present examples verifies experimental results of anti-Cox_B3 of the compounds 1-137 of the present invention, Pleconaril, 3-[3,5-dimethyl-4-[5-(3-methy-1,2-oxazolyl) propoxy]phenyl]-5-(trifluonomethyl) -1,2,4-oxadiazole is used as positive control. Test method is as follows: Vero cells are inoculated into 96well culture plate, and are infected with Cox_B3 virus after 24lin, and then adsorb for 2hr, and then abandon the virus suspension, and then add samples and positive control medications into it according to the above dilution, and then set cells control wells and virus control wells simultaneously, observe the Cytopathic Effect (CPE) of each group when the Cytopathic Effect (CPE) of the virus control group reaches to 4+, and calculate the half-inhibitory concentration (IC50) of these samples for Cox_$_B$3 virus according to Reed-Muench method respectively. The results shows that the compounds of the present invention have excellent anti-coxsackie-viruses activity, and have lower toxicity than the contrast and high safety. Results are listed in Table 2,

TABLE 2

Experimental Results of Anti-Cox_B$_3$ of Compounds 1-137 of the present invention

| Compound No. | Cox_B$_3$ TC$_{50}$ (μg/ml) | IC$_{50}$ (μg/ml) |
|---|---|---|
|  | 50.67 | 0.022 |
| 2 | 58.78 | 0.091 |
| 3 | 36.68 | 0.18 |
| 4 | 35.58 | 0.26 |
| 5 | 40.12 | 0.05 |
| 6 | 48.25 | 0.08 |
| 7 | 36.48 | 0.24 |
| 8 | 52.38 | 0.021 |
| 9 | 48.35 | 0.031 |
| 10 | 46.47 | 0.042 |
| 11 | 45.87 | 0.058 |
| 12 | 40.27 | 0.12 |
| 13 | 38.68 | 0.15 |
| 14 | 40.58 | 0.11 |
| 15 | 42.38 | 0.12 |
| 16 | 41.38 | 0.09 |
| 17 | 44.39 | 0.07 |
| 18 | 37.78 | 0.13 |
| 19 | 35.59 | 0.15 |
| 20 | 35.58 | 0.15 |
| 21 | 34.48 | 0.12 |
| 22 | 40.78 | 0.08 |
| 23 | 39.78 | 0.12 |
| 24 | 42.23 | 0.03 |
| 25 | 40.21 | 0.09 |
| 26 | 38.35 | 0.06 |
| 27 | 39.25 | 0.07 |
| 28 | 32.36 | 0.11 |
| 29 | 33.25 | 0.09 |
| 30 | 34.39 | 0.08 |
| 31 | 36.68 | 0.12 |
| 32 | 40.28 | 0.023 |
| 33 | 35.28 | 0.12 |
| 34 | 33.28 | 0.11 |
| 35 | 36.78 | 0.08 |
| 36 | 40.12 | 0.13 |
| 37 | 42.55 | 0.10 |

TABLE 2-continued

Experimental Results of Anti-Cox_B$_3$
of Compounds 1-137 of the present invention

| Compound No. | Cox_B$_3$ TC$_{50}$ (µg/ml) | IC$_{50}$ (µg/ml) |
|---|---|---|
| 38 | 45.28 | 0.048 |
| 39 | 44.28 | 0.056 |
| 40 | 45.39 | 0.044 |
| 41 | 46.89 | 0.033 |
| 42 | 36.89 | 0.033 |
| 43 | 35.66 | 0.044 |
| 44 | 34.35 | 0.078 |
| 45 | 32.28 | 0.10 |
| 46 | 38.58 | 0.088 |
| 47 | 39.56 | 0.082 |
| 48 | 42.12 | 0.15 |
| 49 | 35.36 | 0.096 |
| 50 | 36.88 | 0.087 |
| 51 | 40.58 | 0.078 |
| 52 | 41.28 | 0.13 |
| 53 | 46.89 | 0.056 |
| 54 | 43.15 | 0.067 |
| 55 | 36.66 | 0.16 |
| 56 | 22.22 | 0.20 |
| 57 | 36.58 | 0.13 |
| 58 | 40.67 | 0.082 |
| 59 | 48.28 | 0.11 |
| 60 | 37.68 | 0.16 |
| 61 | 37.58 | 0.23 |
| 62 | 45.12 | 0.09 |
| 63 | 47.25 | 0.14 |
| 64 | 34.48 | 0.18 |
| 65 | 32.38 | 0.11 |
| 66 | 40.35 | 0.081 |
| 67 | 41.47 | 0.22 |
| 68 | 43.87 | 0.38 |
| 69 | 38.27 | 0.12 |
| 70 | 37.68 | 0.11 |
| 71 | 42.58 | 0.17 |
| 72 | 48.38 | 0.19 |
| 73 | 47.38 | 0.11 |
| 74 | 44.39 | 0.28 |
| 75 | 38.78 | 0.16 |
| 76 | 36.59 | 0.19 |
| 77 | 38.58 | 0.16 |
| 78 | 39.48 | 0.17 |
| 79 | 40.78 | 0.19 |
| 80 | 39.78 | 0.11 |
| 81 | 40.23 | 0.08 |
| 82 | 43.21 | 0.12 |
| 83 | 39.35 | 0.08 |
| 84 | 39.25 | 0.10 |
| 85 | 38.36 | 0.13 |
| 86 | 36.25 | 0.11 |
| 87 | 36.39 | 0.08 |
| 88 | 38.68 | 0.12 |
| 89 | 44.27 | 0.083 |
| 90 | 38.28 | 0.15 |
| 91 | 39.26 | 0.14 |
| 92 | 43.78 | 0.18 |
| 93 | 50.12 | 0.15 |
| 94 | 48.55 | 0.18 |
| 95 | 49.29 | 0.08 |
| 96 | 47.28 | 0.13 |
| 97 | 40.30 | 0.084 |
| 98 | 42.89 | 0.093 |
| 99 | 37.81 | 0.083 |
| 100 | 38.63 | 0.069 |
| 101 | 37.35 | 0.078 |
| 102 | 36.28 | 0.10 |
| 103 | 39.55 | 0.07 |
| 104 | 37.56 | 0.082 |
| 105 | 43.18 | 0.13 |
| 106 | 36.36 | 0.09 |
| 107 | 33.82 | 0.085 |
| 108 | 47.58 | 0.078 |
| 109 | 48.21 | 0.13 |
| 110 | 36.89 | 0.28 |
| 111 | 38.21 | 0.051 |
| 112 | 34.98 | 0.032 |
| 113 | 35.22 | 0.036 |
| 114 | 36.32 | 0.038 |
| 115 | 37.55 | 0.037 |
| 116 | 39.21 | 0.034 |
| 117 | 33.28 | 0.033 |
| 118 | 37.21 | 0.048 |
| 119 | 36.28 | 0.042 |
| 120 | 35.34 | 0.041 |
| 121 | 36.17 | 0.039 |
| 122 | 34.87 | 0.041 |
| 123 | 35.88 | 0.043 |
| 124 | 32.58 | 0.037 |
| 125 | 35.23 | 0.038 |
| 126 | 36.12 | 0.042 |
| 127 | 39.41 | 0.045 |
| 128 | 28.58 | 0.028 |
| 129 | 35.46 | 0.025 |
| 130 | 37.84 | 0.031 |
| 131 | 36.87 | 0.035 |
| 132 | 39.23 | 0.040 |
| 133 | 38.78 | 0.041 |
| 134 | 40.25 | 0.045 |
| 135 | 42.18 | 0.038 |
| 136 | 41.23 | 0.040 |
| 137 | 41.65 | 0.039 |
| Pleconaril | 17.25 | 0.04 |

Explanation: TC50 means half of the toxic concentration; IC50 means half-inhibitory concentration for viruses.

It can be seen from Table 2 that the compounds 1-137 of the present invention have excellent anti-picomaviridae-viruses activity and have lower toxicity and higher safety, comparing with the positive control medication of Pleconaril of 3-[3,5-dimethyl-4-[5-(3-methyl-1,2-oxazoly) propoxy]phenyl]-5-(trifluoromethyl)-1,2,4-oxadiazole.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. An oxadiazole compound having use as anti-coxsackie as represented by formula (I) or pharmaceutically acceptable salt thereof,

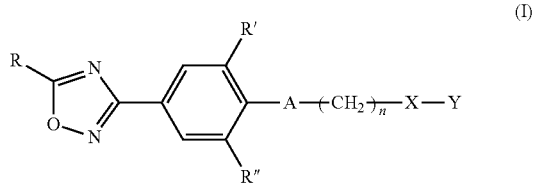

(I)

wherein Y is $C_1$-$C_6$ alkyl, unsubstituted $C_3$-$C_{10}$ cycloalkyl, mono-substituted $C_3$-$C_{10}$ cycloalkyl, disubstituted cycloalkyl, poly-substituted $C_3$-$C_{10}$ cycloalkyl, unsubstituted aryl, mono-substituted aryl, disubstituted aryl, poly-substituted aryl, unsubstituted thienyl, unsubstituted furyl, unsubstituted pyrrolyl, unsubstituted isoxazolyl, unsubstituted oxazolyl, unsubstituted pyridazinyl, unsubstituted pyrazinyl, unsubstituted thiazolyl, unsubstituted isothiazolyl, unsubstituted triazolyl, unsubstituted tetrazolyl, unsubstituted thiadiazolyl, unsubstituted oxadiazolyl, unsubstituted imidazolyl, unsubstituted pyrazolyl, unsubstituted pyridyl, unsubstituted pyrimidinyl, monosubstituted thienyl, monosubstituted furyl, monosubstituted pyrrolyl, monosubstituted isoxazoyl, monosubstituted oxazolyl, monosubstituted pyridazinyl, monosubstituted pyrazinyl, monosubstituted thiazolyl, monosubstituted isothiazolyl, monosubstituted triazolyl, monosubstituted tetrazolyl, monosubstituted thiadiazolyl, monosubstituted oxadiazolyl, monosubstituted imidazolyl, monosubstituted pyrazolyl, monosubstituted pyridyl, mono-substituted pyrimidinyl, disubstituted thienyl, disubstituted furyl, disubstituted pyrrolyl, disubstituted isoxazoly, disubstituted oxazolyl, disubstituted pyridazinyl, disubstituted pyrazinyl, disubstituted thiazolyl, disubstituted isothiazolyl, disubstituted triazolyl, disubstituted imidazolyl, disubstituted pyrazolyl, disubstituted pyrimidinyl, or poly-substituted 5-6 membered heterocyclyl
wherein, R is $CH_3$ or $CF_3$;
R' and R" are methyl;
A is O or S; n=2-3; and,
X is O, S or NH.

2. The oxadiazole compound or pharmaceutically acceptable salt thereof according to claim 1, wherein,
the $C_1$-$C_6$ alkyl is ethyl, propyl, isopropyl or tert-butyl;
the $C_3$-$C_{10}$ cycloalkyl is cyclohexyl or adamantyl;
the monosubstituted phenyl, disubstituted phenyl, polysubstituted phenyl are respectively and independently phenyl substituted by $C_1$-$C_6$ alkyl, phenyl substituted by $C_1$-$C_6$ alkoxy, phenyl substituted by halogen, phenyl substituted by carboxyl, phenyl substituted by ester, phenyl substituted by nitro, phenyl substituted by cyano, or phenyl substituted by trihalomethyl;
the monosubstituted thienyl is thienyl substituted by $C_1$-$C_6$ alkyl; the monosubstituted furyl is furyl substituted by $C_1$-$C_6$ alkyl; the monosubstituted pyrrolyl is pyrrolyl substituted by $C_1$-$C_6$ alkyl; the monosubstituted isoxazolyl is isoxazolyl substituted by $C_1$-$C_6$ alkyl; the monosubstituted oxazolyl is oxazolyl substituted by $C_1$-$C_6$ alkyl; the monosubstituted pyridazinyl is pyridazinyl substituted by $C_1$-$C_6$ alkyl or halogen; the monosubstituted pyrazinyl is pyrazinyl substituted by halogen; the monosubstituted thiazolyl is thiazolyl substituted by $C_1$-$C_6$ alkyl; the monosubstituted isothiazolyl is isothiazolyl substituted by $C_1$-$C_6$ alkyl; the monosubstituted triazolyl is triazolyl substituted by $C_1$-$C_6$ alkyl; the monosubstituted tetrazolyl is tetrazolyl substituted by $C_1$-$C_6$ alkyl;
the monosubstituted thiadiazolyl is thiadiazolyl substituted by $C_1$-$C_6$ alkyl; the monosubstituted oxadiazolyl is oxadiazolyl substituted by $C_1$-$C_6$ alkyl; the monosubstituted imidazolyl is imidazolyl substituted by $C_1$-$C_6$ alkyl; the monosubstituted pyrazolyl is pyrazolyl substituted by $C_1$-$C_6$ alkyl;
the monosubstituted pyridyl is pyridyl substituted by $C_1$-$C_6$ alkyl, pyridyl substituted by $C_1$-$C_6$ alkoxy, pyridyl substituted by halogen, pyridyl substituted by $C_1$-$C_6$ carboxyl, pyridyl substituted by $C_1$-$C_6$ ester group, pyridyl substituted by nitro, pyridyl substituted by cyano or pyridyl substituted by trihalomethyl;
the monosubstituted pyrimidinyl is pyrimidinyl substituted by $C_1$-$C_6$ alkyl, pyrimidinyl substituted by halogen, pyrimidinyl substituted by $C_1$-$C_6$ carboxyl, pyrimidinyl substituted by $C_1$-$C_6$ ester group, pyrimidinyl substituted by hydroxyl, pyrimidinyl substituted by cyano, or pyrimidinyl substituted by trihalomethyl;
the disubstituted thienyl is thienyl disubstituted by halogen; the disubstituted furyl is furyl disubstituted by halogen; the disubstituted pyrrolyl is pyrrolyl disubstituted by halogen; the disubstituted isoxazole is isoxazole disubstituted by halogen; the disubstituted oxazolyl is oxazolyl, disubstituted by halogen; the disubstituted pyridazinyl is pyridazinyl disubstituted by halogen; the disubstituted pyrazinyl is pyrazinyl disubstituted by halogen; the disubstituted thiazolyl is thiazolyl disubstituted by halogen; the disubstituted isothiazolyl is isothiazolyl disubstituted by halogen; the disubstituted triazolyl is triazolyl disubstituted by halogen, disubstituted imidazolyl, disubstituted pyrazolyl.

3. The oxadiazole compound or pharmaceutically acceptable salt thereof according to claim 2, wherein,
the phenyl substituted by $C_1$-$C_6$ alkoxy is phenyl substituted by methoxyl, phenyl substituted by ethoxyl or phenyl substituted by propoxy;
the isoxazolyl substituted by $C_1$-$C_6$ alkyl is isoxazolyl substituted by trifluoromethyl, isoxazolyl substituted by methyl, isoxazolyl substituted by ethyl, isoxazole substituted by propyl or isoxazolyl substituted by isopropyl;
the oxazolyl substituted by $C_1$-$C_6$ alkyl is oxazolyl substituted by methyl;
the pyridazinyl substituted by $C_1$-$C_6$ alkyl is pyridazinyl substituted by methyl or pyridazinyl substituted by ethyl;
the pyrazinyl substituted by halogen is pyrazinyl substituted by fluorine or pyrazinyl substituted by chlorine;
the thiazolyl substituted by $C_1$-$C_6$ alkyl is thiazolyl substituted by methyl, thiazolyl substituted by ethyl, thiazolyl substituted by propyl or thiazolyl substituted by isopropyl;
the isothiazolyl substituted by $C_1$-$C_6$ alkyl is isothiazolyl substituted by methyl, isothiazolyl substituted by ethyl, isothiazolyl substituted by propyl or isothiazolyl substituted by isopropyl;
the triazolyl substituted by $C_1$-$C_6$ alkyl is triazolyl substituted by trifluoromethyl, triazolyl substituted by methyl or triazolyl substituted by ethyl;
the tetrazolyl substituted by $C_1$-$C_6$ alkyl is tetrazolyl substituted by methyl;
the thiadiazolyl substituted by $C_1$-$C_6$ alkyl is thiadiazolyl substituted by trifluoromethyl, thiadiazolyl substituted by methyl, thiadiazolyl substituted by ethyl or thiadiazolyl substituted by propyl;

the oxadiazolyl substituted by $C_1$-$C_6$ alkyl is oxadiazole substituted by trifluoromethyl, oxadiazole substituted by methyl, oxadiazole substituted by ethyl, oxadiazole substituted by propyl;

the imidazolyl substituted by $C_1$-$C_6$ alkyl is imidazolyl substituted by methyl, imidazolyl substituted by ethyl or imidazolyl substituted by propyl;

the pyrazolyl substituted by C1-C6 alkyl is pyrazolyl substituted by trifluoromethyl, pyrazolyl substituted by methyl, pyrazolyl substituted by ethyl or pyrazolyl substituted by propyl.

4. The oxadiazole compound or pharmaceutically acceptable salt thereof according to claim 1, wherein the pharmaceutically acceptable salt is inorganic acid salt, organic acid salt, inorganic alkali salt, or organic alkali salts; the inorganic acid salt is selected from any one of the group consisting of hydrochloride, hydrobromide, hydriodate, sulfate, nitrate, phosphate, perchlorate or the combination thereof; the organic acid salt is selected from any one of the group consisting of tosilate, mesylate, acetate, trifluoroacetate, propionate, citrate, malonate, succinate, lactate, oxalate, tartrate, benzoate or the combination thereof; the inorganic alkali salt is alkaline-earth metal salt; the organic alkali salt is organic amine salt.

5. The oxadiazole compound or pharmaceutically acceptable salt thereof according to claim 4, wherein the alkaline-earth metal salt is magnesium salt or calcium salt; the organic amine salt is morpholine salt, piperidine salt, trialkylamine salt, pyridine salt, dimethylamine salt or diethylamine salt.

6. The oxadiazole compound or pharmaceutically acceptable salt thereof according to claim 1, wherein the oxadiazole compound or pharmaceutically acceptable salt is selected from the group consisting of:
1) 3-[3,5-dimethyl-4-[2-(5-methylisoxazole-3-oxy)ethoxyl]phenyl]-5-(trifluoromethyl)-1,2,4-oxadiazole;
2) 3-[3,5-dimethyl-4[2-(5-methylisoxazole-3-oxy)ethoxyl]phenyl]-5-methyl-1,2,4-oxadiazole;
3) 3-[3,5-dimethyl-4-[2-(5-trifluoromethylisoxazole-3-oxy)ethoxyl]phenyl]-5-(trifluoromethyl)-1,2,4-oxadiazole;
4) 3-[2-[2,6-dimethyl-4-[5-(trifluoromethyl)-1,2,4-oxadiazole-3-yl] phenoxyl] ethoxyl]-isoxazole-5-carboxylate;
5) 3-[3,5-dimethyl-4-[2-(3-trifluoromethylisoxazole-5-oxy)ethoxyl]phenyl]-5-(trifluoromethyl)-1,2,4-oxadiazole;
6) 3-[3,5-dimethyl-4-[3-(5-trifluoromethylisoxazole-3-oxy)propoxy]phenyl]-5-(trifluoromethyl)-1,2,4-oxadiazole;
7) 3-[3-[2,6-dimethyl-4-[5-(trifluoromethyl)-1,2,4-oxadiazole-3-yl] phenoxyl] propoxy]-isoxazolyl-5-carboxylate;
8) 3-[3,5-dimethyl-4-[3-(3-methylisoxazole-5-oxy)propoxy]phenyl]-5-(trifluoromethyl)-1,2,4-oxadiazole;
9) 3-[3,5-dimethyl-4-[3-(3-trifluoromethylisoxazole-5-oxy)propoxy] phenyl]-5-(trifluoromethyl)-1,2,4-oxadiazole;
10) 3-[3,5-dimethyl-4-[2-(5-methylisothiazole-3-oxy)ethoxyl]phenyl]-5-(trifluoromethyl)-1,2,4-oxadiazole;
11) 3-[3,5-dimethyl-4-[3-(5-methylisothiazole-3-oxy)propoxy]phenyl]-5-(trifluoromethyl)-1,2,4-oxadiazole;
12) 3-[3,5-dimethyl-4-[2-(4-methylimidazole-2-oxy)ethoxyl]phenyl]-5-(trifluoromethyl)-1,2,4-oxadiazole;
13) 3-[3,5-dimethyl-4-[2-(4-methylimidazole-2-oxy)ethoxyl]phenyl]-5-(trifluoromethyl)-1,2,4-oxadiazole;
14) 3-[3,5-dimethyl-4-[2-(4-methylthiazole-2-thio)ethoxyl]phenyl]-5-(trifluoromethyl)-1,2,4-oxadiazole;
15) 3-[3,5-dimethyl-4-[2-(3-methyl-1H-pyrazol-5-oxy)ethoxyl]phenyl]-5-(trifluoromethyl)-1,2,4-oxadiazole;
16) 3-[3,5-dimethyl-4-[2-[1-methyl-3-(trifluoromethyl)-1H-pyrazol-5-oxy]ethoxyl]phenyl]-5-(trifluoromethyl)-1,2,4-oxadiazole;
17) 5-[2-[2,6-dimethyl-4-[5-(trifluoromethyl)-1,2,4-oxadiazole-3-yl] phenoxyl] ethoxyl]-1-methyl-1H-pyrazol-3-carboxylic acid;
18) 3-[3,5-dimethyl-4[(2-(5-methyl-1H-imidazole-2-thio)ethoxyl]phenyl]-5-(trifluoromethyl)-1,2,4-oxadiazole;
19) 3-[2-[2,6-dimethyl-4-[5-(trifluoromethyl)-1,2,4-oxadiazole-3-yl]phenoxyl] ethoxyl]-5-methyl-1,2,4-oxadiazole;
20) 3-[3-[2,6-dimethyl-4-[5-(trifluoromethyl)-1,2,4-oxadiazole-3-yl]phenoxyl] propoxy]-5-methyl-1,2,4-oxadiazole;
21) 3-[3,5-dimethyl-4-[(4-(trifluoromethyl)-1,2,4-oxadiazole-2-oxy)ethoxyl]phenyl]-5-(trifluoromethyl)-1,2,4-oxadiazole;
22) 5-[3,5-dimethyl-4-[(2-(5-(trifluoromethyl)-1,2,4-oxadiazole-3-oxy)ethoxyl]phenyl]-3-(trifluoromethyl)-1,2,4-oxadiazole;
23) 3-[3,5-dimethyl-4[(2-(3-methyl-1,2,4-thiadiazole-5-thio)ethoxyl] phenyl]-5-(trifluoromethyl)-1,2,4-oxadiazole;
24) 3-[2-[2,6-dimethyl-4-[5-(trifluoromethyl)-1,2,4-oxadiazole-3-yl]phenoxyl]ethoxyl]-5-methyl-4H-1,2,4-triazole;
25) 3-[2-[2,6-dimethyl-4-[5-(trifluoromethyl)-1,2,4-oxadiazole-3-yl]phenoxyl] ethylthio]-5-methyl-4H-1,2,4-triazole;
26) 3-[2-[2,6-dimethyl-4-[5-(trifluoromethyl)-1,2,4-oxadiazole-3-yl] phenoxyl]ethylthio]-5-trifluoromethyl-4H-1,2,4-triazole;
27) 3-[2-[2,6-dimethyl-4-[5-(trifluoromethyl)-1,2,4-oxadiazole-3-yl]phenoxyl]ethylthio]-4,5-dimethyl-4H-1,2,4-triazole;
28) 3-[3,5-dimethyl-4-[2-[5-methyl-1,3,4-oxadiazole-2-oxy]ethoxyl]phenyl]-5-(trifluoromethyl)-1,2,4-oxadiazole;
29) 3-[3,5-dimethyl-4-[3-[5-methyl-1,3,4-oxadiazole-2-oxy]propylthio]phenyl]-5-(trifluoromethyl)-1,2,4-oxadiazole;
30) 3-[3,5-dimethyl-4-[2-[5-trifluoromethyl-1,3,4-thiadiazole-2-oxy]ethoxyl]phenyl]-5-(trifluoromethyl)-1,2,4-oxadiazole;
31) 3-[3,5-dimethyl-4-[2-[5-trifluoromethyl-1,3,4-thiadiazole-2-oxy]ethylthio] phenyl]-5-(trifluoromethyl)-1,2,4-oxadiazole;
32) 2-[2-[2,6-dimethyl-4-[5-(trifluoromethyl)-1,2,4-oxadiazole-3-yl]phenoxyl] ethoxyl]-4-hydroxyl-pyrimidine-5-carboxylic acid;
33) 2-[2-[2,6-dimethyl-4-[5-(trifluoromethyl)-1,2,4-oxadiazole-3-yl]phenoxyl] ethoxyl]-4-(trifluoromethyl) pyrimidine;
34) 2-[2-[2,6-dimethyl-4-[5-(trifluoromethyl)-1,2,4-oxadiazole-3-yl]phenoxyl] ethylthio]-4-(trifluoromethyl) pyrimidine;
35) 3-[3,5-dimethyl-4-[(2-(cyclohexyloxy)ethoxyl)phenyl]-5-(trifluoromethyl)-1,2,4-oxadiazole;
36) 3-[3,5-dimethyl-4-[(2-tert-butoxy)ethoxyl]phenyl]-5-(trifluoromethyl)-1,2,4-oxadiazole;
37) 3-[3,5-dimethyl-4-[(2-adamantanoxy)propoxy]phenyl]-5-(trifluoromethyl)-1,2,4-oxadiazole;
38) 4-[2,6-dimethyl-4-[(5-(trifluoromethyl)-1,2,4-oxadiazole-3-yl)phenoxyl] ethoxyl]-3-fluorobenzonitrile;

39) 3-[3,5-dimethyl-4-[(2-fluoro-4-methylphenoxy) ethoxyl]phenyl]-5-(trifluoromethyl)-1,2,4-oxadiazole;
40) 3-[3,5-dimethyl-4-[(2-fluoro-4-methoxyphenoxyl) ethoxyl]phenyl]-5-(trifluoromethyl)-1,2,4-oxadiazole;
41) 3-[3,5-dimethyl-4-[(2-fluoro-4-nitrophenoxy) ethoxyl]phenyl]-5-(trifluoromethyl)-1,2,4-oxadiazole;
42) 3-[3,5-dimethyl-4-[(2,6-dichlorophenoxy)ethoxyl] phenyl]-5-(trifluoromethyl)-1,2,4-oxadiazole;
43) 3-[3,5-dimethyl-4-[(2,4-dichlorophenoxy)ethoxyl] phenyl]-5-(trifluoromethyl)-1,2,4-oxadiazole;
44) 6-[2,6-dimethyl-4-[(5-(trifluoromethyl)-1,2,4-oxadiazole-3-yl)phenoxyl]ethoxyl] pyridine-2-oxy-ethylketoxime;
45) 5-[2,6-dimethyl-4-[(5-(trifluoromethyl)-1,2,4-oxadiazole-3-yl)phenoxyl] ethoxyl]pyridine-2-oxy-ethylketoxime;
46) 6-[2,6-dimethyl-4-[(5-(trifluoromethyl)-1,2,4-oxadiazole-3-yl)phenoxyl] ethoxyl]-5-fluoro-3-cyanopyridine;
47) 2-[2,6-dimethyl-4-[(5-(trifluoromethyl)-1,2,4-oxadiazole-3-yl)phenoxyl] ethoxyl]-3-fluoro-5-methylpyridine;
48) 6-[2,6-dimethyl-4-[(5-(trifluoromethyl)-1,2,4-oxadiazole-3-yl)phenoxyl] ethoxyl]-5-fluoro-2-hydroxy-3-cyanopyridine;
49) 6-[2,6-dimethyl-4-[(5-(trifluoromethyl)-1,2,4-oxadiazole-3-yl) phenoxyl] ethoxyl]-5-fluoro-3-pyridinecarboxylate;
50) 6-[2,6-dimethyl-4-[(5-(trifluoromethyl)-1,2,4-oxadiazole-3-yl) phenoxyl] ethoxyl]-3-cyanopyridine;
51) 6-[2,6-dimethyl-4-[(5-(trifluoromethyl)-1,2,4-oxadiazole-3-yl) phenoxyl] ethoxyl]-5-methylpyridine;
52) 6-[2,6-dimethyl-4-[(5-(trifluoromethyl)-1,2,4-oxadiazole-3-yl) phenoxyl] ethoxyl]-5-trifluoromethylpyridine;
53) 4-[2,6-dimethyl-4-[(5-(trifluoromethyl)-1,2,4-oxadiazole-3-yl) phenoxyl] ethoxyl]-2-hydroxyl-5-fluoropyrimidine;
54) 4-[2,6-dimethyl-4-[(5-(trifluoromethyl)-1,2,4-oxadiazole-3-yl) phenoxyl] ethoxyl]-2-methoxyl-5-fluoropyrimidine;
55) 3-[2-(2,6-dimethyl-4-[(5-(trifluoromethyl)-1,2,4-oxadiazole-3-yl)phenoxyl] ethoxyl]-2-formamide-6-fluoropyrazine;
56) 3-[2,6-dimethyl-4-[(5-(trifluoromethyl)-1,2,4-oxadiazole-3-yl)phenoxyl] ethoxyl]-6-methylpyridazine;
57) 3-[3,5-dimethyl-4-[2-(5-trifluoromethylisoxazole-3-oxy)ethoxyl]phenyl]-5-(trifluoromethyl)-1,2,4-oxadiazole;
58) 3-[2-[2,6-dimethyl-4-[5-(trifluoromethyl)-1,2,4-oxadiazole-3-yl] phenoxyl] ethoxyl]isoxazole-5-carboxylate;
59) 3-[3,5-dimethyl-4-[2-(3-trifluoromethylisoxazole-5-oxy) ethoxyl]phenyl]-5-(trifluoromethyl)-1,2,4-oxadiazole;
60) 3-[3,5-dimethyl-4-[3-(5-trifluoromethylisoxazole-3-oxy) propoxy]phenyl]-5-(trifluoromethyl)-1,2,4-oxadiazole;
61) 3-[3-[2,6-dimethyl-4-[5-(trifluoromethyl)-1,2,4-oxadiazole-3-yl] phenoxyl] propoxy]isoxazole-5-carboxylate;
62) 3-[3,5-dimethyl-4-[3-(3-methylisoxazole-5-oxy) propoxy] phenyl]-5-(trifluoromethyl)-1,2,4-oxadiazole;
63) 3-[3,5-dimethyl-4-[3-(3-trifluoromethylisoxazole-5-oxy) propoxy] phenyl]-5-(trifluoromethyl)-1,2,4-oxadiazole;
64) 3-[3,5-dimethyl-4-[2-(5-methylisothiazole-3-oxy) ethoxyl]phenyl]-5-(trifluoromethyl)-1,2,4-oxadiazole;
65) 3-[3,5-dimethyl-4-[3-(5-methylisothiazole-3-oxy) propoxy]phenyl]-5-(trifluoromethyl)-1,2,4-oxadiazole;
66) 3-[3,5-dimethyl-4-[2-(4-methylimidazole-2-oxy) ethoxyl] phenyl]-5-(trifluoromethyl)-1,2,4-oxadiazole;
67) 3-[3,5-dimethyl-4-[2-(4-methylthiazole-2-oxy) ethoxyl ]phenyl]-5-(trifluoromethyl)-1,2,4-oxadiazole;
68) 3-[3,5-dimethyl-4-[2-(4-methylthiazole-2-thio) ethoxyl] phenyl]-5-(trifluoromethyl)-1,2,4-oxadiazole;
69) 3-[3,5-dimethyl-4-[2-(3-methyl-1H-pyrazol-5-oxy) ethoxyl] phenyl]-5-(trifluoromethyl)-1,2,4-oxadiazole;
70) 3-[3,5-dimethyl-4-[2-[1-methyl-3-(trifluoromethyl)-1H-pyrazol-5-oxy]ethoxyl] phenyl]-5-(trifluoromethyl)-1,2,4-oxadiazole;
71) 5-[2-[2,6-dimethyl-4-[5-(trifluoromethyl)-1,2,4-oxadiazole-3-yl]phenoxyl] ethoxyl]-1-methyl-1H-pyrazole-3-carboxylic acid;
72) 3-[3,5-dimethyl-4-[2-(5-methyl-1H-imidazole-2-oxy) ethoxyl]phenyl]-5-(trifluoromethyl)-1,2,4-oxadiazole;
73) 3-[2-[2,6-dimethyl-4-[5-(trifluoromethyl)-1,2,4-oxadiazole-3-yl]phenoxyl] ethoxyl]-5-methyl-1,2,4-oxadiazole;
74) 3-[3-[2,6-dimethyl-4-[5-(trifluoromethyl)-1,2,4-oxadiazole-3-yl]phenoxyl] propoxy]-5-methyl-1,2,4-oxadiazole;
75) 3-[3,5-dimethyl-4-[(4-(trifluoromethyl)-1,2,4-oxadiazole-2-oxy)ethoxyl] phenyl]-5-(trifluoromethyl)-1,2,4-oxadiazole;
76) 5-[3,5-dimethyl-4-[2-(5-(trifluoromethyl)-1,2,4-oxadiazole-3-oxy)ethoxyl] phenyl]-5-(trifluoromethyl)-1,2,4-oxadiazole;
77) 3-[3,5-dimethyl-4-[2-(3-methyl-1,2,4-thiadiazole-5-thio) ethoxyl]phenyl]-5-(trifluoromethyl)-1,2,4-oxadiazole;
78) 3-[2-[2,6-dimethyl-4-[5-(trifluoromethyl)-1,2,4-oxadiazole-3-yl]phenoxyl] ethoxyl]-5-methyl-4H-1,2,4-triazole;
79) 3-[2-[2,6-dimethyl-4-[5-(trifluoromethyl)-1,2,4-oxadiazole-3-yl]phenoxyl] ethylthio]-5-methyl-4H-1,2,4-triazole;
80) 3-[2-[2,6-dimethyl-4-[5-(trifluoromethyl)-1,2,4-oxadiazole-3-yl]phenoxyl] ethylthio]-5-trifluoromethyl-4H-1,2,4-triazole;
81) 3-[2-[2,6-dimethyl-4-[(5-(trifluoromethyl)-1,2,4-oxadiazole-3-yl]phenoxyl] ethylthio]-4,5-dimethyl-4H-1,2,4-triazole;
82) 3-[3,5-dimethyl-4-[2-[5-methyl-1,3,4-oxadiazole-2-oxy]ethoxyl] phenyl]-5-(trifluoromethyl)-1,2,4-oxadiazole;
83) 3-[3,5-dimethyl-4-[3-[5-methyl-1,3,4-oxadiazole-2-oxy]propylthio]phenyl]-5-(trifluoromethyl)-1,2,4-oxadiazole;
84) 3-[3,5-dimethyl-4-[2-[5-trifluoromethyl-1,3,4-thiadiazole-2-oxy]ethoxyl] phenyl]-5-(trifluoromethyl)-1,2,4-oxadiazole;
85) 3-[3,5-dimethyl-4-[2-[5-trifluoromethyl-1,3,4-thiadiazole-2-oxy]ethylthio] phenyl]-5-(trifluoromethyl)-1,2,4-oxadiazole;
86) 2-[2-[2,6-dimethyl-4-[5-(trifluoromethyl)-1,2,4-oxadiazole-3-yl]phenoxyl] ethoxyl]-4-hydroxyl-pyrimidine-5-carboxylic acid;
87) 2-[2-[2,6-dimethyl-4-[5-(trifluoromethyl)-1,2,4-oxadiazole-3-yl]phenoxyl] ethoxyl]-4-(trifluoromethyl)pyrimidine;

88) 2-[2-[2,6-dimethyl-4-[5-(trifluoromethyl)-1,2,4-oxadiazole-3-yl]phenoxyl] ethylthio]-4-(trifluoromethyl) pyrimidine;
89) 3-[3,5-dimethyl-4-[2-(cyclohexyloxy)ethoxyl]phenyl]-5-(trifluoromethyl)-1,2,4-oxadiazole;
90) 3-[3,5-dimethyl-4-[(2-tert-butoxy)ethoxyl]phenyl]-5-(trifluoromethyl)-1,2,4-oxadiazole;
91) 3-[3,5-dimethyl-4-[(2-adamantanoxy)propoxy]phenyl]-5-(trifluoromethyl)-1,2,4-oxadiazole;
92) 4-[2,6-dimethyl-4-[(5-(trifluoromethyl)-1,2,4-oxadiazole-3-yl)phenoxyl] ethoxyl]-3-fluorobenzonitrile;
93) 3-[3,5-dimethyl-4-[(2-fluoro-4-methylphenoxy) ethoxyl]phenyl]-5-(trifluoromethyl)-1,2,4-oxadiazole;
94) 3-[3,5-dimethyl-4-[(2-fluoro-4-methoxyphenoxy) ethoxyl]phenyl]-5-(trifluoromethyl)-1,2,4-oxadiazole;
95) 3-[3,5-dimethyl-4-[(2-fluoro-4-nitrophenoxy) ethoxyl]phenyl]-5-(trifluoromethyl)-1,2,4-oxadiazole;
96) 3-[3,5-dimethyl-4-[(2,6-dichlorophenoxy)ethoxyl] phenyl]-5-(trifluoromethyl)-1,2,4-oxadiazole;
97) 3-[3,5-dimethyl-4-[(2,4-dichlorophenoxy)ethoxyl] phenyl]-5-(trifluoromethyl)-1,2,4-oxadiazole;
98) 6-[2,6-dimethyl-4-[(5-(trifluoromethyl)-1,2,4-oxadiazole-3-yl)phenoxyl]ethoxyl]pyridine-2-oxy-ethylketoxime;
99) 5-[2,6-dimethyl-4-[(5-(trifluoromethyl)-1,2,4-oxadiazole-3-yl)phenoxyl] ethoxyl]pyridine-2-oxy-ethylketoxime;
100) 6-[2,6-dimethyl-4-[(5-(trifluoromethyl)-1,2,4-oxadiazole-3-yl) phenoxyl] ethoxyl]-5-fluoro-3-cyanopyridine;
101) 2-[2,6-dimethyl-4-[(5-(trifluoromethyl)-1,2,4-oxadiazole-3-yl) phenoxyl] ethoxyl]-3-fluoro-5-methylpyridine;
102) 6-[2,6-dimethyl-4-[(5-(trifluoromethyl)-1,2,4-oxadiazole-3-yl) phenoxyl] ethoxyl]-5-fluoro-2-hydroxyl-3-cyanopyridine;
103) 6-[2,6-dimethyl-4-[(5-(trifluoromethyl)-1,2,4-oxadiazole-3-yl) phenoxyl] ethoxyl]-5-fluoro-3-pyridinecarboxylate;
104) 6-[2,6-dimethyl-4-[(5-(trifluoromethyl)-1,2,4-oxadiazole-3-yl) phenoxyl] ethoxyl]-3-cyanopyridine;
105) 6-[2,6-dimethyl-4-[(5-(trifluoromethyl)-1,2,4-oxadiazole-3-yl) phenoxyl] ethoxyl]-5-methylpyridine;
106) 6-[2,6-dimethyl-4-[(5-(trifluoromethyl)-1,2,4-oxadiazole-3-yl) phenoxyl] ethoxyl]-5-trifluoromethylpyridine;
107) 4-[2,6-dimethyl-4-(5-(trifluoromethyl)-1,2,4-oxadiazole-3-yl) phenoxyl] ethoxyl]-2-hydroxy-5-fluoropyrimidine;
108) 4-[2,6-dimethyl-4-[(5-(trifluoromethyl)-1,2,4-oxadiazole-3-yl) phenoxyl] ethoxyl]-2-methoxyl-5-fluoropyrimidine;
109) 3-[2-(2,6-dimethyl-4-[(5-(trifluoromethyl)-1,2,4-oxadiazole-3-yl) phenoxyl] ethoxyl]-2-formamide-6-fluoropyrazine;
110) 3-[2,6-dimethyl-4-[(5-(trifluoromethyl)-1,2,4-oxadiazole-3-yl)phenoxyl] ethoxyl]-6-methylpyridazine;
111) 3-[3,5-dimethyl-4-[2-[4-(5-methyl-1,2,4-oxadiazole-3-yl) phenoxyl]ethoxyl] phenyl]-5-(trifluoromethyl)-1,2,4-oxadiazole;
112) 3-[3,5-dimethyl-4-[2-[4-[5-(trifluoromethyl)-1,2,4-oxadiazole-3-yl]phenoxyl]ethoxyl]phenyl]-5-(trifluoromethyl)-1,2,4-oxadiazole;
113) 2-[2-[2,6-dimethyl-4-[5-(trifluoromethyl)-1,2,4-oxadiazole-3-yl]phenoxyl] ethoxyl]-5-(5-methyl-1,2,4-oxadiazole-3-yl)-pyridine;
114) 2-[2-[2,6-dimethyl-4-[5-(trifluoromethyl)-1,2,4-oxadiazole-3-yl]phenoxyl] ethoxyl]-5-[5-(trifluoromethyl)-1,2,4-oxadiazole-3-yl]-pyridine;
115) 2-[2-[2,6-dimethyl-4-[5-(trifluoromethyl)-1,2,4-oxadiazole-3-yl]phenoxyl] ethoxyl]-3-fluoro-5-(5-methyl-1,2,4-oxadiazole-3-yl)-pyridine;
116) 2-[2-[2,6-dimethyl-4-[5-(trifluoromethyl)-1,2,4-oxadiazole-3-yl]phenoxyl] ethoxyl]-3-fluoro-5-[5-(trifluoromethyl)-1,2,4-oxadiazole-3-yl]-pyridine;
117) 3-[3,5-dimethyl-4-[3-[4-(5-methyl-1,2,4-oxadiazole-3-yl]phenoxyl]propoxy]phenyl]-5-(trifluoromethyl)-1,2,4-oxadiazole;
118) 3-[3,5-dimethyl-4-[3-[4-[5-(trifluoromethyl)-1,2,4-oxadiazole-3-yl]phenoxyl] propoxy]phenyl]-5-(trifluoromethyl)-1,2,4-oxadiazole;
119) 2-[3-[2,6-dimethyl-4-[5-(trifluoromethyl)-1,2,4-oxadiazole-3-yl]phenoxyl] propoxy]-5-(5-methyl-1,2,4-oxadiazole-3-yl)-pyridine;
120) 2-[3-[2,6-dimethyl-4-[5-(trifluoromethyl)-1,2,4-oxadiazole-3-yl]phenoxyl] propoxy]-3-fluoro-5-[5-(trifluoromethyl)-1,2,4-oxadiazole-3-yl]-pyridine;
121) 2-[3-[2,6-dimethyl-4-[5-(trifluoromethyl)-1,2,4-oxadiazole-3-yl]phenoxyl] propoxy]-3-fluoro-5-(5-methyl-1,2,4-oxadiazole-3-yl)-pyridine;
122) 2-[3-[2,6-dimethyl-4-[5-(trifluoromethyl)-1,2,4-oxadiazole-3-yl]phenoxyl] propoxy]-3-fluoro-5-[5-(trifluoromethyl)-1,2,4-oxadiazole-3-yl]-pyridine;
123) 3-[4-[2-[2-fluoro-4-[5-(trifluoromethyl)-1,2,4-oxadiazole-3-yl]phenoxyl]ethoxy]-3,5-dimethyl-phenyl]-5-[5-(trifluoromethyl)-1,2,4-oxadiazole;
124) 3-[4-[3-[2-fluoro-4-[5-(trifluoromethyl)-1,2,4-oxadiazole-3-yl]phenoxyl]propoxy]-3,5-dimethyl-phenyl]-5-[5-(trifluoromethyl)-1,2,4-oxadiazole;
125) 3-[3,5-dimethyl-4-[3-[5-(5-methylthiophene-2-oxy) phenoxyl]propoxy]phenyl]-5-(trifluoromethyl)-1,2,4-oxadiazole;
126) 3-[3,5-dimethyl-4-[3-[5-(5-methylfuran-2-oxy)phenoxyl] propoxy]phenyl]-5-(trifluoromethyl)-1,2,4-oxadiazole;
127) 3-[3,5-dimethyl-4-[3-[5-(5-methylpyrrole-2-oxy) phenoxyl] propoxy]phenyl]-5-(trifluoromethyl)-1,2,4-oxadiazole;
128) 5-[2-[2,6-dimethyl-4-[5-(trifluoromethyl)-1,2,4-oxadiazole-3-yl] phenoxyl]ethoxyl]-1-methyl-tetrazole;
129) 3-[4-[3-[3,4-dimethylcyclohexyloxy]propoxy]-3,5-dimethylphenyl]-5-(trifluoromethyl)-1,2,4-oxadiazole;
130) 3-[4-[3-[2,6-dichloro-4-methylphenoxy]propoxy]-3,5-dimethylphenyl]-5-(trifluoromethyl)-1,2,4-oxadiazole;
131) 2-cyano-5-[3-[2,6-dimethyl-4-[5-(trifluoromethyl)-1,2,4-oxadiazole-3-yl]phenoxyl]propoxy] pyrazine;
132) 2-[3-[2,6-dimethyl-4-[5-(trifluoromethyl)-1,2,4-oxadiazole-3-yl]phenoxyl]propoxy]-5-cyano-pyrimidine;
133) 3-cyano-6-[3-[2,6-dimethyl-4-[5-(trifluoromethyl)-1,2,4-oxadiazole-3-yl]phenoxyl]propoxy] pyridazine;
134) 2-[3-[2,6-dimethyl-4-[5-(trifluoromethyl)-1,2,4-oxadiazole-3-yl]phenoxyl]propoxy]-5-nitropyridine;
135) 2-[5-(trifluoromethyl)-1,2,4-oxadiazole-3-yl]-5-[3-[2,6-dimethyl-4-[5-(trifluoromethyl)-1,2,4-oxadiazole-3-yl]phenoxyl]propoxy] pyrazine;
136) 2-[3-[2,6-dimethyl-4-[5-(trifluoromethyl)-1,2,4-oxadiazole-3-yl]phenoxyl]propoxy]-5-[5-(trifluoromethyl)-1,2,4-oxadiazole-3-yl]-pyrimidine; and
137) 3-[5-(trifluoromethyl)-1,2,4-oxadiazole-3-yl]-6-[3-[2,6-dimethyl-4-[5-(trifluoromethyl)-1,2,4-oxadiazole-3-yl]phenoxyl]propoxy] pyridazine.

7. A pharmaceutical composition, comprising a therapeutically effective amount of oxadiazole compound or a pharmaceutically acceptable salt thereof according to claim 1, and pharmaceutically acceptable carriers.

8. The pharmaceutical composition according to claim 7, wherein the pharmaceutical composition comprising 1-99 wt. % of the oxadiazole compound or the pharmaceutically acceptable salt thereof, and 1-99 wt. % of pharmaceutically acceptable carriers.

9. The pharmaceutical composition according to claim 7, wherein the pharmaceutically acceptable carriers are selected from the group consisting of antioxidant, bacteriostatic agent, pH regulating agent, buffer agent, emulsifying agent, and solubilizer; wherein the antioxidant is sodium thiosulfate, sodium sulfite, sodium hydrogen sulfite, sodium bisulfite, dibutyl benzoic acid and sodium metabisulfite; the bacteriostatic agent is 0.5 wt. % phenol, 0.3 wt. % cresol or 0.5wt. % trichloro-tert-butanol; the pH regulating agent is hydrochloric acid, citric acid, potassium hydroxide, sodium hydroxide or sodium citrate; the buffer agent is sodium dihydrogen phosphate or disodiun hydrogen phosphate; the emulsifying agent is polysorbate-80, sorbitan oleate, polyoxyethylene-polyoxypropylene block copolymer, lecithin or soybean lecithin; the solubilizer is 2[2-[3,4-bis(2-hydroxyethoxy)oxolan-2-yl]-2-hydroxyethoxy)ethoxy]ethyl octadec-9-enoate or glycerol.

10. The pharmaceutical composition according to claim 7, wherein the therapeutically effective amount is 10-500 mg per day.

11. The pharmaceutical composition according to claim 8, wherein the pharmaceutical composition comprises 5-75 wt. % of the oxadiazole compound or the pharmaceutically acceptable salt thereof, and 25-95 wt % of pharmaceutically acceptable carriers.

12. The pharmaceutical composition according to claim 10, wherein the therapeutically effective amount is 20-300 mg per day.

* * * * *